(12) United States Patent
Zavoronkovs et al.

(10) Patent No.: US 11,008,303 B2
(45) Date of Patent: May 18, 2021

(54) TLR 9 INHIBITORS

(71) Applicant: Insilico Medicine IP Limited

(72) Inventors: Aleksandrs Zavoronkovs, Pak Shek Kok (HK); Vladimir Aladinskiy, Pak Shek Kok (HK); Aleksandr Aliper, Moscow (RU)

(73) Assignee: Insilico Medicine IP Limited, Hong Kong (HK)

( * ) Notice: Subject to any disclaimer, the term of this patent is extended or adjusted under 35 U.S.C. 154(b) by 0 days.

(21) Appl. No.: 16/889,462

(22) Filed: Jun. 1, 2020

(65) Prior Publication Data

US 2020/0290994 A1 Sep. 17, 2020

Related U.S. Application Data

(60) Continuation-in-part of application No. 16/861,142, filed on Apr. 28, 2020, which is a division of application No. 16/262,631, filed on Jan. 30, 2019, now Pat. No. 10,689,360.

(51) Int. Cl.
    *C07D 401/12* (2006.01)
    *C07D 401/14* (2006.01)

(52) U.S. Cl.
    CPC ......... *C07D 401/12* (2013.01); *C07D 401/14* (2013.01)

(58) Field of Classification Search
    CPC .................................................. C07D 401/12
    USPC ....................................... 514/307
    See application file for complete search history.

(56) References Cited

FOREIGN PATENT DOCUMENTS

| WO | 2002020484 A1 | 3/2002 |
|---|---|---|
| WO | 2008152471 A1 | 12/2008 |
| WO | 2015057655 A1 | 4/2015 |
| WO | 2016195194 A2 | 12/2016 |
| WO | 2017106607 A1 | 6/2017 |
| WO | 2019125849 A1 | 6/2019 |
| WO | 2020020800 A1 | 1/2020 |

OTHER PUBLICATIONS

International Search Report and Written Opinion for PCT/IB2020/050583 dated Apr. 26, 2020.

*Primary Examiner* — Taofiq A Solola
(74) *Attorney, Agent, or Firm* — Maschoff Brennan; Jonathan M. Benns

(57) ABSTRACT

A method for inhibiting TLR9 includes contacting the TLR9 with compound of general formula (I):

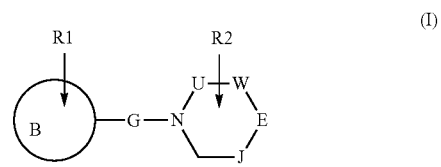

wherein the meanings of the variables are explained in the specification,
or a stereoisomeric form or a mixture of stereoisomeric forms, or pharmaceutically acceptable salts thereof. A pharmaceutical composition can include compounds of the invention, which can be used in a method for inhibiting TLR9 activity in vitro or in vivo. The method can be performed by administering the compound to a subject to inhibit TLR9 activity, which can be used to treat a disease or disorder associated with TLR9.

21 Claims, No Drawings

TLR 9 INHIBITORS

CROSS-REFERENCE

This patent application is a continuation-in-part of U.S. application Ser. No. 16/861,142 filed Apr. 28, 2020, which is a divisional of U.S. application Ser. No. 16/262,631 filed Jan. 30, 2019, which applications are incorporated herein by specific reference in their entirety.

BACKGROUND

Technical Field

The present invention relates to novel compounds, which are useful as Toll-like receptor ("TLR") inhibitors, and in particular, TLR9 inhibitors. Provided herein are novel compounds, compositions comprising such compounds, method for preparation thereof and methods of their use. The invention relates to pharmaceutical compositions containing at least one compound according to the invention that are useful for the treatment of conditions related to TLR9 inhibition, such as inflammatory and/or autoimmune diseases, and methods of inhibiting the activity of TLR9 in a subject.

Background Art

Toll-like receptors (TLRs) represent transmembrane proteins that detect invading pathogens by binding pathogen derived molecules and that induce signaling cascades for proinflammatory gene expression. More precisely, TLRs recognize highly conserved structural motifs known as pathogen-associated microbial patterns (PAMPs), which are exclusively expressed by microbial pathogens, or danger-associated molecular patterns (DAMPs) that are endogenous molecules released from necrotic or dying cells. This includes intracellular proteins such as heat shock proteins as well as protein fragments from the extracellular matrix (McCarthy C. et al, "Toll-like receptors and damage-associated molecular patterns: novel links between inflammation and hypertension" Am. J. Physiol. Heart. Circ. Physiol., 2014, 15 January; 306(2):H184-96).

The TLRs were reported as a key component of innate and adaptive immunity (Pasare C., et al (2005) "Toll-Like Receptors: Linking Innate and Adaptive Immunity". In: Gupta S., Paul W. E., Steinman R. (eds) Mechanisms of Lymphocyte Activation and Immune Regulation X. Advances in Experimental Medicine and Biology, vol 560. Springer, Boston, Mass.).

Upon PAMP recognition, the TLR typically induces intracellular signaling cascades. An inflammatory response for a short duration can be beneficial because it helps to clear the infectious agent. However, prolonged inflammation is not desirable due to possible tissue damage. Indeed, excessive production of inflammatory cytokines and chemokines via TLR pathways is often associated with many inflammatory-associated and autoimmune diseases. Therefore, fine control of inflammation in the TLR pathway is highly desirable for effective host defense.

TLR9 are expressed in immune system cells, such as dendritic cells, macrophages, natural killer cells, and other antigen presenting cells. The TLR9 preferentially binds DNA present in bacteria and viruses, and triggers signaling cascades that lead to pro-inflammatory cytokine responses. Additionally, cancer, infection, and tissue damage can all modulate TLR9 expression and activity. TLR9 is a factor in autoimmune diseases, where TLR9 antagonists can help regulate autoimmune inflammation.

Additionally, TLR9 expression may be higher in breast cancer, ovarian cancer, prostate cancer, non-small cell lung cancer, and glioma. Accordingly, inhibiting TLR9 may be used to inhibit these cancers or others. TLR9 may play a role in non-viral cancers TLR9 antagonists can be used to inhibit TLR9 recognition of specific unmethylated CpG oligonucleotides (ODN) that distinguish microbial DNA from mammalian DNA. As such, TLR9 antagonists can neutralize the stimulatory effect of CpG ODNs. This inhibition can inhibit the inflammatory response or associated inflammatory disorder. A TLR9 antagonist can be used as a therapeutic agent for CpG-ODN-mediated over-inflammatory responses, and may also be used to treat autoimmune diseases.

Previously, some TLR9 inhibitors have been known to be unselective because they inhibit multiple types of TLRs. For example, WO2020/020800 teaches compounds that inhibit TLR7, TLR8, and TLR9. Additionally, WO2008/152471 teaches another type of compound that also inhibits TLR7, TLR8, and TLR9. As a result, the compounds recited in these reference cannot selectively inhibit TLR9.

TLRs are expressed on many types of cancer cells. During chronic inflammation, abnormal activation of TLRs in normal fibroblasts and epithelial cells might facilitate neoplastic transformation and carcinogenesis. Cancer cells activated by TLR signals can release cytokines and chemokines that recruit and optimize immune cells to release further cytokines and chemokines. The result is an aberrant cytokine profile associated with immune tolerance, cancer progression and propagation of the tumor microenvironment (Sato Y. et al, "Cancer Cells Expressing Toll-like Receptors and the Tumor" Cancer Microenviron. 2009 September; 2(Suppl 1): 205-214).

Concluding, excessive TLR activation can affect the immune system homeostasis by excessive pro-inflammatory cytokines and chemokines production, and consequently is responsible for the development of many inflammatory and autoimmune diseases, such as systemic lupus, infection-associated sepsis, atherosclerosis, and asthma, and cancer deceases. It is therefore believed that inhibitors/antagonists targeting TLR signals may be beneficial to treat these disorders.

Thus, it is desirable to regulate the pro-inflammatory and anti-inflammatory cytokines and chemokines in the TLR-mediated pathways. Therefore, the technical problem to be solved by the present invention is to provide a new type of effective TLR9 inhibitor that can be used during treatment of, inter alia, autoimmune deceases, inflammatory diseases and cancer diseases.

SUMMARY

In some embodiments, a method for inhibiting TLR9 activity, the method comprising: administering a compound to a TLR9 in an amount sufficient to inhibit activity thereof, the compound having a structure of Formula (I), or a stereoisomeric form, a mixture of stereoisomeric forms, or pharmaceutically acceptable salts thereof,

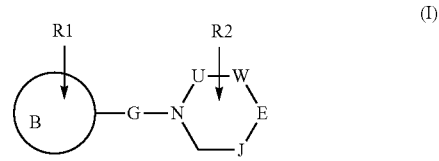

wherein, ring B is a substituted monocycle containing 3-7 atoms, the monocycle being selected from an aryl or heteroaryl, wherein the heteroaryl has from 1 to 4 heteroatoms, which are independently selected from nitrogen, oxygen, and sulfur;

G represents a substituted or unsubstituted $C_0$-$C_5$ alkylene;

one of W, U, E and J represents CR-T and the rest of W, U, and J are independently absent or independently represent $CR_2$ or NR; T represents:

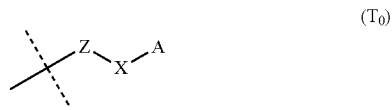

(T₀)

wherein,

Z is an amide in either orientation, which can be selected from:

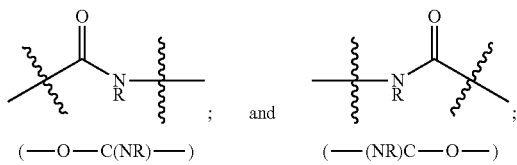

(—O—C(NR)—)     (—(NR)C—O—)

X represents $(-CH_2-)_n$ wherein n=1 to 12, thereby forming an alkylene chain, wherein the alkylene chain is optionally substituted with halogen, $C_1$-$C_{20}$ alkyl, $C_2$-$C_{10}$ alkenyl, $C_2$-$C_{10}$ alkynyl, halogenated $C_1$-$C_{10}$ alkyl, hydroxy $C_1$-$C_{10}$ alkyl, or $C_1$-$C_{10}$alkoxy;

A is 3 to 8 membered heterocyclyl fused with an aryl or heteroaryl, which can be unsubstituted or substituted with one or more R substituents;

$R_1$ is one or more of, independently of each other, H, halogen, halogenated $C_1$-$C_{10}$ alkyl, hydroxy $C_1$-$C_{10}$ alkyl, $C_1$-$C_{10}$ alkoxy, or —CN;

$R_2$ is one or more of, independently of each other, H, $C_1$-$C_{20}$ alkyl, halogenated $C_1$-$C_{20}$ alkyl, —OR, —SR, or —CN; and each R is independently H, $C_1$-$C_{20}$ alkyl, $C_2$-$C_{20}$ alkenyl, $C_2$-$C_{20}$ alkynyl, hydroxy $C_1$-$C_{10}$ alkyl, $C_1$-$C_{10}$ alkoxy, halogenated $C_1$-$C_{20}$ alkyl, halogen, —OH, —$NO_2$, —CN, —COOH, —CHO, —$SO_3H$, —$SO_2R$, —SOR, —$NH_2$, —NHR, —$NR_2$, $CHal_3$, —NHCO($C_1$-$C_{10}$)alkyl, —CONHR, —C(O)R, —$CO_2R$, —C(O)N(R)₂, —NRC(O)R, —NRC(O)N(R)₂, —$NRSO_2R$.

In some embodiments, the method includes inhibiting TLR9 activity with the compound.

In some embodiments, the method includes contacting cells with the compound, wherein the cells express the TLR9.

In some embodiments, the compound is administered to the TLR9 in vitro.

In some embodiments, the compound is administered to the TLR9 in vivo.

In some embodiments, the compound is administered to a subject having the TLR9, wherein the subject is susceptible or has a disease or disorder mediated by the TLR9. In some aspects, the subject has a includes at least one of: a disorder or disease associated with the over-stimulation of the subject's immune system by microbes; interferon-mediated diseases; or inflammatory cytokine-mediated inflammation diseases. In some aspects, the method includes treating the disorder or disease associated with the over-stimulation of the subject's immune system by microbes. In some aspects, the method includes treating the interferon-mediated disease. In some aspects, the method includes treating the inflammatory cytokine-mediated inflammation diseases. In some aspects, the method includes treating at least one of: antiphospholipid syndrome, autoimmune hepatitis, autoimmune myocarditis, autoimmune orchitis, autoimmune pancreatitis, autoimmune retinopathy, rheumatoid arthritis, psoriatic arthritis, osteoarthritis, systemic Lupus Erythematosus, lupus nephritis, osteoporosis, systemic sclerosis, multiple sclerosis, psoriasis, diabetes, inflammatory bowel disease (Crohn's Disease and Ulcerative Colitis), Hyperimmunoglobulinemia D, periodic fever syndrome, systemic juvenile idiopathic arthritis, sepsis, atherosclerosis, Celiac disease, Sjogren's Syndrome, Alzheimer's disease, Parkinson's disease, or cancer. In some aspects, the cancer is selected from colorectal cancer, breast cancer, ovarian carcinoma, pancreatic cancer, lung cancer, renal cell carcinoma, cervical cancer and multiple myeloma. In some aspects, the method includes inhibiting inflammation in the subject with the compound. In some aspects, the method includes inhibiting activation of an immune system of the subject with the compound.

In some embodiments, the compounds are selective for TLR9. In some instances, the selectivity for TLR9 is compared to a TLR7 or TLR8. In some instances, the selectivity for TLR9 is compared to other receptors. In some instances, the selectivity for TLR9 is compared to other TLRs. Thus, the compounds can selectivity target and inhibit a TLR9 over other types of receptors.

In some embodiments, the method is performed with a compound having a structure of Formula (III), or a stereoisomeric form, a mixture of stereoisomeric forms, or pharmaceutically acceptable salts thereof,

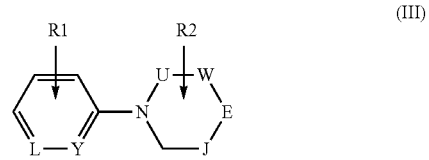

(III)

wherein,

Y and L are independently CR or CH, one of W, U, E and J represents CH(T) and the rest of W, U, and J are independently absent or independently represent $CH_2$;

T represents:

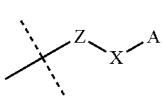

(T₀)

wherein,

Z is an amide in either orientation, which can be selected from:

(—O—C(NR)—) ; and (—(NR)C—O—) ;

X represents (—CH$_2$—)$_n$ wherein n=1 to 24, thereby forming an alkylene chain, wherein the alkylene chain is optionally substituted with halogen, C$_1$-C$_{20}$ alkyl, C$_2$-C$_{10}$ alkenyl, C$_2$-C$_{10}$ alkynyl, halogenated C$_1$-C$_{10}$ alkyl, hydroxy C$_1$-C$_{10}$ alkyl, or C$_1$-C$_{10}$alkoxy;

A represents:

A1

A2

A3

A4 any one of A1, A2, A3, or A4 is unsubstituted or substituted with one or more R groups;

R$_1$ is one or more of, independently of each other, H, halogen, halogenated C$_1$-C$_{10}$ alkyl, hydroxy C$_1$-C$_{10}$ alkyl, C$_1$-C$_{10}$ alkoxy, or —CN;

R$_2$ is one or more of, independently of each other, H, C$_1$-C$_{20}$ alkyl, halogenated C$_1$-C$_{20}$ alkyl, —OR, —SR, or —CN; and each R is independently H, C$_1$-C$_{20}$ alkyl, C$_2$-C$_{20}$ alkenyl, C$_2$-C$_{20}$ alkynyl, hydroxy C$_1$-C$_{10}$ alkyl, alkoxy, halogenated C$_1$-C$_{20}$ alkyl, halogen, —OH, —NO$_2$, —CN, —COOH, —CHO, —SO$_3$H, —SO$_2$R, —SOR, —NH$_2$, —NHR, —NR$_2$, CHal$_3$, —NHCO(C$_1$-C$_{10}$)alkyl (e.g., alkyl-amide), —CONHR, —C(O)R, —CO$_2$R, —C(O)N(R)$_2$, —NRC(O) R, —NRC(O)N(R)$_2$, —NRSO$_2$R.

In some aspects, Y is CR and L is CH, R$_1$ is para position;

one of W, U, E and J represents CH(T) and the rest of W, U, and J are independently absent or independently represent CH$_2$;

X represents (—CH$_2$—)$_n$ wherein n=1, 2, or 3, thereby forming an alkylene chain;

A represents:

A1

A1 is unsubstituted or substituted with one or more R groups;

R$_1$ is one or more of, independently of each other, H, halogen, halogenated C$_1$-C$_{10}$ alkyl, hydroxy C$_1$-C$_{10}$ alkyl, C$_1$-C$_{10}$ alkoxy, or —CN;

R$_2$ is one or more of, independently of each other, H, C$_1$-C$_{20}$ alkyl, halogenated C$_1$-C$_{20}$ alkyl, —OR, —SR, or —CN; and each R is independently H, C$_1$-C$_{20}$ alkyl, C$_2$-C$_{20}$ alkenyl, C$_2$-C$_{20}$ alkynyl, hydroxy C$_1$-C$_{10}$ alkyl, C$_1$-C$_{10}$ alkoxy, halogenated C$_1$-C$_{20}$ alkyl, halogen, —OH, —NO$_2$, —CN.

In some embodiments, the compound has a structure of Formula (IV), or a stereoisomeric form, a mixture of stereoisomeric forms, or pharmaceutically acceptable salts thereof, (IV)

wherein,

Y and L are independently CH or CR, wherein at least one of Y or L is CH;

G1 is CH$_2$ or absent;

each R is independently selected from H, halogen, C$_1$-C$_6$ alkyl, halogenated C$_1$-C$_6$ alkyl, hydroxy C$_1$-C$_6$ alkyl, C$_1$-C$_6$ alkoxy, or —CN; and X represents (—CH$_2$—)$_n$, wherein n=2 or 3, thereby forming an alkylene chain.

In some embodiments, the compound has a structure of Formula (VI), or a stereoisomeric form, a mixture of stereoisomeric forms, or pharmaceutically acceptable salts thereof, (VI)

wherein,

G1 is CH or absent;

X represents (—CH$_2$—)$_n$ wherein n=1 to 4, thereby forming an alkylene chain, the alkylene chain is optionally substituted with halogen, C$_1$-C$_6$ alkyl, C$_2$-C$_8$ alkenyl, C$_3$-C$_8$ cycloalkyl, C$_2$-C$_8$ alkynyl, halogenated C$_1$-C$_6$ alkyl, hydroxy C$_1$-C$_6$ alkyl, or C$_1$-C$_6$ alkoxy;

R3 is one or more of H, halogen, halogenated C$_1$-C$_{10}$ alkyl, hydroxy C$_1$-C$_{10}$ alkyl, C$_1$-C$_{10}$ alkoxy, or —CN;

R4 is one or more of H, halogen, halogenated C$_1$-C$_{10}$ alkyl, hydroxy C$_1$-C$_{10}$ alkyl, C$_1$-C$_{10}$ alkoxy, or —CN;

R5 is one or more of H, halogen, halogenated C$_1$-C$_{10}$ alkyl, hydroxy C$_1$-C$_{10}$ alkyl, or C$_1$-C$_{10}$ alkoxy.

In some aspects: G1 is CH or absent; X represents (—CH$_2$—)$_n$ wherein n=2 or 3, thereby forming an alkylene chain; R3 is —CN; R4 is one or more of H, halogen, or halogenated C$_1$-C$_{10}$ alkyl; and R5 is one or more of H, hydroxy C$_1$-C$_{10}$ alkyl, or C$_1$-C$_{10}$ alkoxy.

In some embodiments, the compound is selected from:

Compound 1

Compound 4

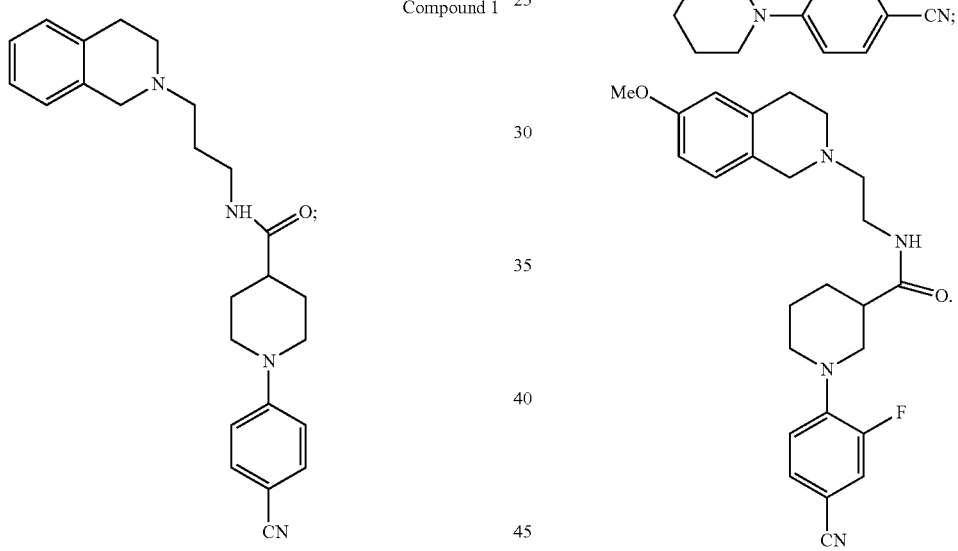

Compound 9

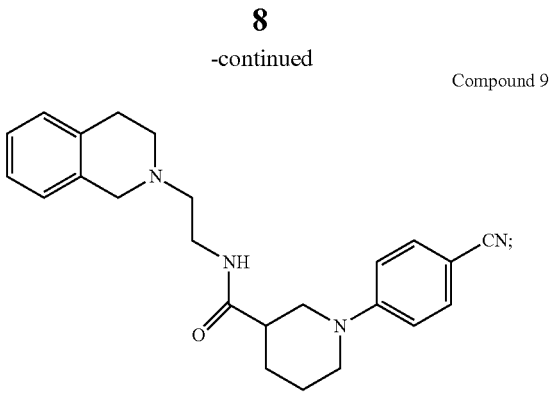

Compound 15

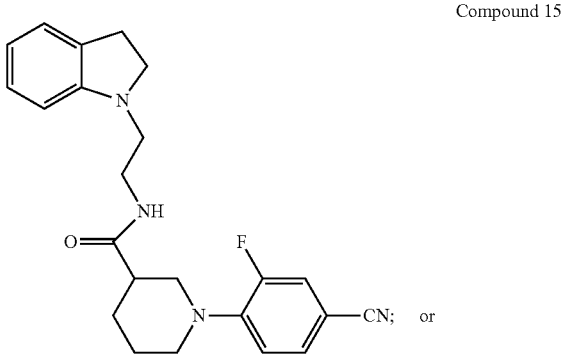

Compound 25

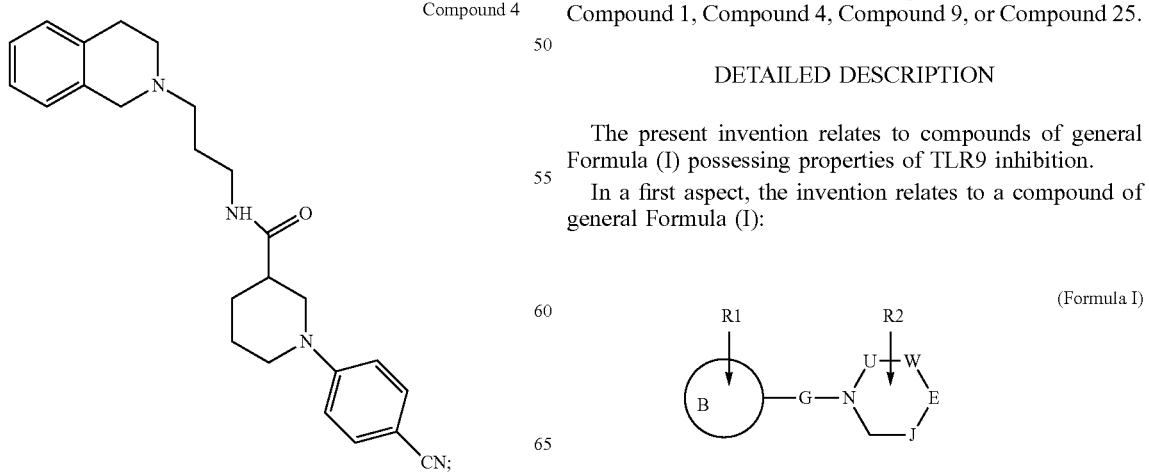

In some embodiments, the compound is selected from: Compound 1, Compound 4, Compound 9, or Compound 25.

DETAILED DESCRIPTION

The present invention relates to compounds of general Formula (I) possessing properties of TLR9 inhibition.

In a first aspect, the invention relates to a compound of general Formula (I):

(Formula I)

wherein,
ring B is a substituted or unsubstituted monocycle containing 3-7 atoms, the monocycle being selected from a cycloalkyl, aryl, heterocyclyl or heteroaryl,
wherein the heterocyclyl or heteroaryl has from 1 to 4 heteroatoms, which are independently selected from nitrogen, oxygen, and sulfur;
G represents a substituted or unsubstituted $C_0$-$C_5$ alkylene;
one of W, U, E and J represents CR-T or N-T and the rest of W, U, and J are independently absent or independently represent $CR_2$, NR or S;
T represents:

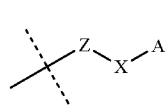
(T₀)

wherein,
Z is selected from —O—C(O)—, —(O)C—O—, —N—C(O)—, —(O)C—N—, —O—C(NR)—, —(NR)C—O—, —O—C(S)—, —(S)C—O—, —C(O)—, —C(O)ON—, and —N—C(O)—O—;
X represents (—CH₂—)$_n$ wherein n=1 to 24, thereby forming an alkylene chain, wherein the carbon atoms of the alkylene chain can be replaced by at least one heteroatom, wherein the heteroatoms are independently —O—, —S— or —NH—, with the proviso that each heteroatom is separated from each other heteroatom by at least one carbon atom; the alkylene chain is optionally substituted with halogen, $C_1$-$C_{20}$ alkyl, $C_2$-$C_{10}$ alkenyl, $C_2$-$C_{10}$ alkynyl, halogenated $C_1$-$C_{10}$ alkyl, hydroxy $C_1$-$C_{10}$ alkyl, or $C_1$-$C_{10}$ alkoxy;
A is 3 to 8 membered cycloalkyl, heterocyclyl, aryl or heteroaryl, which can be unsubstituted or substituted with one or more R substituents,
$R_1$ is one or more of, independently of each other, H, $C_1$-$C_{20}$ alkyl, $C_2$-$C_{10}$ alkenyl, $C_2$-$C_{10}$ alkynyl, halogen, halogenated $C_1$-$C_{10}$ alkyl, hydroxy $C_1$-$C_{10}$ alkyl, $C_1$-$C_{10}$ alkoxy, —CN, a 3-8 membered saturated or partially unsaturated carbocyclic ring, a 3-7 membered heterocyclic ring having 1-4 heteroatoms that are independently selected from nitrogen, oxygen, or sulfur, or a 5-6 membered monocyclic heteroaryl ring having 1-4 heteroatoms that are independently selected from nitrogen, oxygen, or sulfur;
$R_2$ is one or more of, independently of each other, H, $C_1$-$C_{20}$ alkyl, halogenated $C_1$-$C_{20}$ alkyl, —OR, —SR, —CN, a 3-8 membered saturated or partially unsaturated carbocyclic ring, a 3-7 membered heterocyclic ring having 1-4 heteroatoms that are independently selected from nitrogen, oxygen, or sulfur, or a 5-6 membered monocyclic heteroaryl ring having 1-4 heteroatoms that are independently selected from nitrogen, oxygen, or sulfur; and
each R is independently H, $C_1$-$C_{20}$ alkyl, $C_2$-$C_{20}$ alkenyl, $C_2$-$C_{20}$ alkynyl, hydroxy $C_1$-$C_{10}$ alkyl, $C_1$-$C_{10}$ alkoxy, halogenated $C_1$-$C_{20}$ alkyl, halogen, —OH, —NO₂, —CN, —COOH, —CHO, —SO₃H, —SO₂R, —SOR, —NH₂, —NHR, —NR₂, CHal₃, —NHCO($C_1$-$C_{10}$)alkyl (e.g., alkylamide), —CONHR, —C(O)R, —CO₂R, —C(O)N(R)₂, —NRC(O)R, —NRC(O)N(R)₂, —NRSO₂R; a 3-8 membered saturated or partially unsaturated cycloalkyl, $C_{3-10}$ aryl, a 3-7 membered heterocyclic ring having 1-4 heteroatoms that are independently selected from nitrogen, oxygen, or sulfur, or a 5-6 membered heteroaryl having 1-4 heteroatoms that are independently selected from nitrogen, oxygen, or sulfur, or two R groups together, if present, form 3-8 membered saturated or unsaturated carbocyclic or heterocyclic ring which contains at least one heteroatom selected from N, S and O, or a stereoisomeric form or a mixture of stereoisomeric forms, or pharmaceutically acceptable salts thereof.

Preferably, both ring B and the ring formed by N, Y, W, E, J and C are monocycle rings, i.e. they are not condensed with other saturated or unsaturated rings.

With regard to Formula I, the TLR9 antagonist can include:
ring B is a substituted monocycle containing 3-7 atoms, the monocycle being selected from an aryl or heteroaryl, wherein the heteroaryl has from 1 to 4 heteroatoms, which are independently selected from nitrogen, oxygen, and sulfur;
G represents a substituted or unsubstituted $C_0$-$C_5$ alkylene;
one of W, U, E and J represents CR-T and the rest of W, U, and J are independently absent or independently represent $CR_2$ or NR;
T represents:

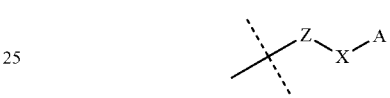
(T₀)

wherein,
Z is selected from —O—C(NR)— or —(NR)C—O—;
X represents (—CH₂—)$_n$ wherein n=1 to 24, thereby forming an alkylene chain, wherein the alkylene chain is optionally substituted with halogen, $C_1$-$C_{20}$ alkyl, $C_2$-$C_{10}$ alkenyl, $C_2$-$C_{10}$ alkynyl, halogenated $C_1$-$C_{10}$ alkyl, hydroxy $C_1$-$C_{10}$ alkyl, or $C_1$-$C_{10}$ alkoxy;
A is 3 to 8 membered heterocyclyl fused with an aryl or heteroaryl, which can be unsubstituted or substituted with one or more R substituents;
$R_1$ is one or more of, independently of each other, H, halogen, halogenated $C_1$-$C_{10}$ alkyl, hydroxy $C_1$-$C_{10}$ alkyl, $C_1$-$C_{10}$ alkoxy, or —CN;
$R_2$ is one or more of, independently of each other, H, $C_1$-$C_{20}$ alkyl, halogenated $C_1$-$C_{20}$ alkyl, —OR, —SR, or —CN; and
each R is independently H, $C_1$-$C_{20}$ alkyl, $C_2$-$C_{20}$ alkenyl, $C_2$-$C_{20}$ alkynyl, hydroxy $C_1$-$C_{10}$ alkyl, $C_1$-$C_{10}$ alkoxy, halogenated $C_1$-$C_{20}$ alkyl, halogen, —OH, —NO₂, —CN, —COOH, —CHO, —SO₃H, —SO₂R, —SOR, —NH₂, —NHR, —NR₂, CHal₃, —NHCO($C_1$-$C_{10}$)alkyl (e.g., alkylamide), —CONHR, —C(O)R, —CO₂R, —C(O)N(R)₂, —NRC(O)R, —NRC(O)N(R)₂, —NRSO₂R;
or a stereoisomeric form or a mixture of stereoisomeric forms, or pharmaceutically acceptable salts thereof.

In the second aspect, the invention relates to a compound of formula (I) characterized in that the compound is a compound of general formula (II):

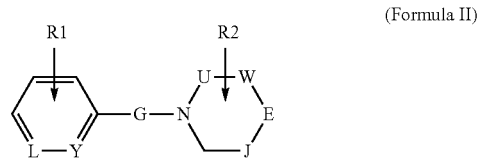
(Formula II)

wherein,
Y and L are independently CR or N; or one of Y and L is absent, one of W, U, E and J represents —CH(T)- or N-T and the rest of W, U, E and J are independently absent or independently represent $CR_2$, NR or S;

G represents an unsubstituted $C_0$-$C_5$ alkylene;

T represents:

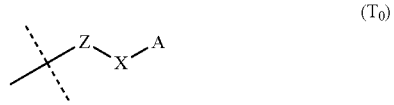

wherein,

Z is selected from —O—C(O)—, —(O)C—O—, —N—C(O)—, —(O)C—N—, —O—C(NR)—, —(NR)C—O—, —O—C(S)—, —(S)C—O—, —C(O)—, —C(O)ON—, and —N—C(O)—O—;

X represents (—$CH_2$—)$_n$ wherein n=1 to 12, thereby forming an alkylene chain, wherein the carbon atoms of the alkylene chain can be replaced by at least one heteroatom, wherein the heteroatoms are independently —O—, —S— or —NH—, with the proviso that each heteroatom is separated from each other heteroatom by at least one carbon atom; the alkylene chain is optionally substituted with a halogen, $C_1$-$C_{20}$ alkyl, $C_2$-$C_{10}$ alkenyl, $C_2$-$C_{10}$ alkynyl, halogenated $C_1$-$C_{10}$ alkyl, hydroxy $C_1$-$C_{10}$ alkyl, or $C_1$-$C_{10}$alkoxy;

A is 3-8 membered substituted or unsubstituted cycloalkyl, heterocyclyl, aryl or heteroaryl, $R_1$ is one or more of, independently of each other, H, $C_1$-$C_{12}$ alkyl, $C_2$-$C_{10}$ alkenyl, $C_2$-$C_{10}$ alkynyl, F, Cl, halogenated $C_1$-$C_4$ alkyl, hydroxy $C_1$-$C_4$ alkyl, $C_1$-$C_4$ alkoxy, or —CN;

$R_2$ is one or more of, independently of each other, H, $C_1$-$C_{20}$ alkyl, halogenated $C_1$-$C_{20}$ alkyl, —OR, —SR, or —CN; and each R is independently H, $C_1$-$C_{10}$ alkyl, $C_2$-$C_{10}$ alkenyl, $C_2$-$C_{10}$ alkynyl, hydroxy $C_1$-$C_{10}$ alkyl, $C_1$-$C_{10}$ alkoxy, halogenated $C_1$-$C_{20}$ alkyl, halogen, —OH, —$NO_2$, —CN, —COOH, —CHO, —$SO_3$H, —$SO_2$R, —SOR, —$NH_2$, —NHR, —$NR_2$, —$CHal_3$, —NHCO($C_1$-$C_{10}$)alkyl (alkylamide), —CONHR, —C(O)R, —$CO_2$R, —C(O)N(R)$_2$, —NRC(O)R, —NRC(O)N(R)$_2$, —$NRSO_2$R; a 3-8 membered saturated or partially unsaturated cycloalkyl, $C_{3-10}$ aryl, a 3-7 membered heterocylic ring having 1-4 heteroatoms that are independently selected from nitrogen, oxygen, or sulfur, or a 5-6 membered heteroaryl having 1-4 heteroatoms that are independently selected from nitrogen, oxygen, or sulfur, or two R groups together, if present, form 3-8 membered saturated or unsaturated carbocyclic or heterocyclic ring which contains at least one heteroatom selected from N, S and O;

or a stereoisomeric form or a mixture of stereoisomeric forms, or pharmaceutically acceptable salts thereof.

With regard to Formula II, the TLR9 antagonist can include:

Y and L are independently CR or N,

G represents a substituted or unsubstituted $C_0$-$C_5$ alkylene;

one of W, U, E and J represents CH(T) and the rest of W, U, and J are independently absent or independently represent $CR_2$ or NR;

X represents (—$CH_2$—)$_n$ wherein n=1 to 24, thereby forming an alkylene chain, wherein the alkylene chain is optionally substituted with halogen, $C_1$-$C_{20}$ alkyl, $C_2$-$C_{10}$ alkenyl, $C_2$-$C_{10}$ alkynyl, halogenated $C_1$-$C_{10}$ alkyl, hydroxy $C_1$-$C_{10}$ alkyl, or $C_1$-$C_{10}$alkoxy;

A is 3 to 8 membered heterocyclyl fused with an aryl or heteroaryl, which can be unsubstituted or substituted with one or more R substituents, $R_1$ is one or more of, independently of each other, H, halogen, halogenated $C_1$-$C_{10}$ alkyl, hydroxy $C_1$-$C_{10}$ alkyl, $C_1$-$C_{10}$ alkoxy, or —CN;

$R_2$ is one or more of, independently of each other, H, $C_1$-$C_{20}$ alkyl, halogenated $C_1$-$C_{20}$ alkyl, —OR, —SR, or —CN; and each R is independently H, $C_1$-$C_{20}$ alkyl, $C_2$-$C_{20}$ alkenyl, $C_2$-$C_{20}$ alkynyl, hydroxy $C_1$-$C_{10}$ alkyl, $C_1$-$C_{10}$ alkoxy, halogenated $C_1$-$C_{20}$ alkyl, halogen, —OH, —$NO_2$, —CN, —COOH, —CHO, —$SO_3$H, —$SO_2$R, —SOR, —$NH_2$, —NHR, —$NR_2$, $CHal_3$, —NHCO($C_1$-$C_{10}$)alkyl (e.g., alkylamide), —CONHR, —C(O)R, —$CO_2$R, —C(O)N(R)$_2$, —NRC(O)R, —NRC(O)N(R)$_2$, —$NRSO_2$R;

or a stereoisomeric form or a mixture of stereoisomeric forms, or pharmaceutically acceptable salts thereof.

In further aspect, the compound of the invention is characterized in that the compound is a compound of general formula (III):

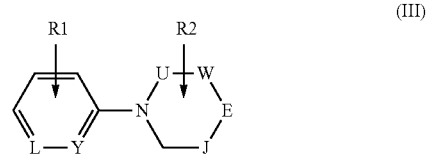

wherein,

Y and L are independently CR or N; or optionally one of Y and L is absent, one of W, U, E and J represents —CH(T)- or N-T and the rest of W, U, E and J are independently absent or independently represent $CR_2$, NR or S;

G represents an unsubstituted $C_0$-$C_5$ alkylene;

T represents:

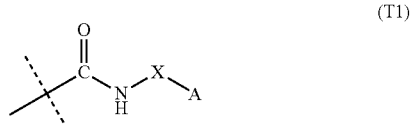

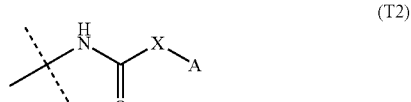

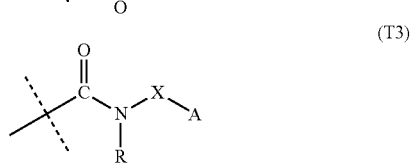

wherein,

X represents —($CH_2$—)$_n$ wherein n=1 to 6, thereby forming an alkylene chain, wherein the carbon atoms of the alkylene chain can be replaced by at least one heteroatom, wherein the heteroatoms are independently —O—, —S— or —NH—, with the proviso that each heteroatom is separated from each other heteroatom by at least one carbon atom; the alkylene chain is optionally substituted with a halogen, $C_1$-$C_{20}$ alkyl, $C_2$-$C_{10}$ alkenyl, $C_2$-$C_{10}$ alkynyl, halogenated $C_1$-$C_{10}$ alkyl, hydroxy $C_1$-$C_{10}$alkyl; or $C_1$-$C_{10}$alkoxy;

A is 3 to 8 membered substituted or unsubstituted cycloalkyl, heterocyclyl, aryl or heteroaryl, $R_1$ is one or more of, independently of each other, H, $C_1$-$C_{12}$ alkyl, $C_2$-$C_{10}$ alkenyl, $C_2$-$C_{10}$ alkynyl, F, Cl, halogenated $C_1$-$C_4$alkyl, hydroxy $C_1$-$C_4$alkyl, $C_1$-$C_4$alkoxy, or —CN;

$R_2$ is one or more of, independently of each other, H, $C_1$-$C_{20}$ alkyl, halogenated $C_1$-$C_{20}$ alkyl, —OR, —SR, or —CN; and each R is independently H, $C_1$-$C_{10}$ alkyl, $C_2$-$C_{10}$ alkenyl, $C_2$-$C_{10}$ alkynyl, hydroxy $C_1$-$C_{10}$ alkyl, $C_1$-$C_{10}$ alkoxy, halogenated $C_1$-$C_{20}$ alkyl, halogen, —OH, —NO$_2$, —CN, —COOH, —CHO, —SO$_3$H, —SO$_2$R, —SOR, —NH$_2$, —NHR, —NR$_2$, —CHal$_3$, —NHCO($C_1$-$C_{10}$)alkyl, —CONHR, —C(O)R, —CO$_2$R, —C(O)N(R)$_2$, —NRC(O)R, —NRC(O)N(R)$_2$, —NRSO$_2$R; a 3-8 membered saturated or partially unsaturated cycloalkyl, $C_{3-10}$ aryl, a 3-7 membered heterocylic ring having 1-4 heteroatoms that are independently selected from nitrogen, oxygen, or sulfur, or a 5-6 membered heteroaryl having 1-4 heteroatoms that are independently selected from nitrogen, oxygen, or sulfur, or two R groups together, if present, form 3-8 membered saturated or unsaturated carbocyclic or heterocyclic ring which contains at least one heteroatom selected from N, S and O;

or a stereoisomeric form or a mixture of stereoisomeric forms, or pharmaceutically acceptable salts thereof.

With regard to Formula III, the TLR9 antagonist can include:

Y and L are independently CR or CH, one of W, U, E and J represents CH(T) and the rest of W, U, and J are independently absent or independently represent CH$_2$;

X represents (—CH$_2$—)$_n$ wherein n=1 to 24, thereby forming an alkylene chain, wherein the alkylene chain is optionally substituted with halogen, $C_1$-$C_{20}$ alkyl, $C_2$-$C_{10}$ alkenyl, $C_2$-$C_{10}$ alkynyl, halogenated $C_1$-$C_{10}$ alkyl, hydroxy $C_1$-$C_{10}$ alkyl, or $C_1$-$C_{10}$alkoxy;

A is 3 to 8 membered heterocyclyl fused with an aryl or heteroaryl, which can be unsubstituted or substituted with one or more R substituents, $R_1$ is one or more of, independently of each other, H, halogen, halogenated $C_1$-$C_{10}$ alkyl, hydroxy $C_1$-$C_{10}$ alkyl, $C_1$-$C_{10}$ alkoxy, or —CN;

$R_2$ is one or more of, independently of each other, H, $C_1$-$C_{20}$ alkyl, halogenated $C_1$-$C_{20}$ alkyl, —OR, —SR, or —CN; and each R is independently H, $C_1$-$C_{20}$ alkyl, $C_2$-$C_{20}$ alkenyl, $C_2$-$C_{20}$ alkynyl, hydroxy $C_1$-$C_{10}$ alkyl, $C_1$-$C_{10}$ alkoxy, halogenated $C_1$-$C_{20}$ alkyl, halogen, —OH, —NO$_2$, —CN, —COOH, —CHO, —SO$_3$H, —SO$_2$R, —SOR, —NH$_2$, —NHR, —NR$_2$, —CHal$_3$, —NHCO($C_1$-$C_{10}$)alkyl (e.g., alkylamide), —CONHR, —C(O)R, —CO$_2$R, —C(O)N(R)$_2$, —NRC(O)R, —NRC(O)N(R)$_2$, —NRSO$_2$R;

or a stereoisomeric form or a mixture of stereoisomeric forms, or pharmaceutically acceptable salts thereof.

With regard to Formula III, the TLR9 antagonist can include:

Y and L are independently CR or CH, one of W, U, E and J represents CH(T) and the rest of W, U, and J are independently absent or independently represent CH$_2$;

X represents (—CH$_2$—)$_n$ wherein n=1 to 24, thereby forming an alkylene chain, wherein the alkylene chain is optionally substituted with halogen, $C_1$-$C_{20}$ alkyl, $C_2$-$C_{10}$ alkenyl, $C_2$-$C_{10}$ alkynyl, halogenated $C_1$-$C_{10}$ alkyl, hydroxy $C_1$-$C_{10}$ alkyl, or $C_1$-$C_{10}$alkoxy;

A is 3 to 8 membered heterocyclyl fused with an aryl or heteroaryl, which can be unsubstituted or substituted with one or more R substituents, $R_1$ is one or more of, independently of each other, H, halogen, halogenated $C_1$-$C_{10}$ alkyl, hydroxy $C_1$-$C_{10}$ alkyl, $C_1$-$C_{10}$ alkoxy, or —CN;

$R_2$ is one or more of, independently of each other, H, $C_1$-$C_{20}$ alkyl, halogenated $C_1$-$C_{20}$ alkyl, —OR, —SR, or —CN; and each R is independently H, $C_1$-$C_{20}$ alkyl, $C_2$-$C_{20}$ alkenyl, $C_2$-$C_{20}$ alkynyl, hydroxy $C_1$-$C_{10}$ alkyl, $C_1$-$C_{10}$ alkoxy, halogenated $C_1$-$C_{20}$ alkyl, halogen, —OH, —NO$_2$, —CN, —COOH, —CHO, —SO$_3$H, —SO$_2$R, —SOR, —NH$_2$, —NHR, —NR$_2$, —CHal$_3$, —NHCO($C_1$-$C_{10}$)alkyl (e.g., alkylamide), —CONHR, —C(O)R, —CO$_2$R, —C(O)N(R)$_2$, —NRC(O)R, —NRC(O)N(R)$_2$, —NRSO$_2$R;

or a stereoisomeric form or a mixture of stereoisomeric forms, or pharmaceutically acceptable salts thereof.

In yet another aspect, the invention relates to a compound of formula (III) as defined herein, wherein in the formula (III) with the definitions provided herein, the T represents:

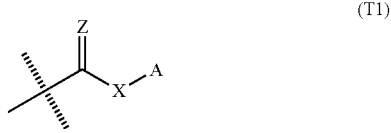

(T1)

or a stereoisomeric form or a mixture of stereoisomeric forms, or pharmaceutically acceptable salts thereof.

In a further aspect of the present invention, in the formula (III), as defined herein, the T represents:

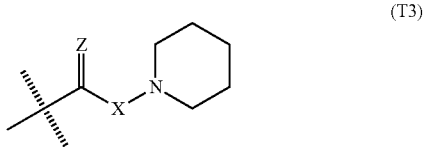

(T3)

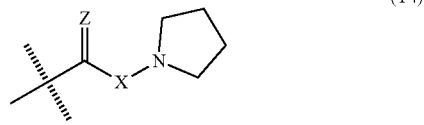

(T4)

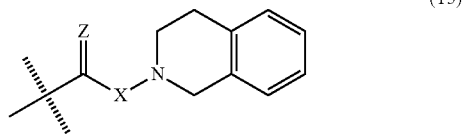

(T5)

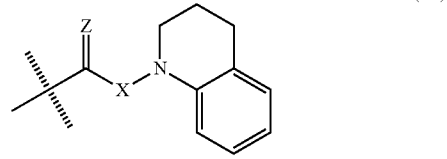

(T6)

wherein any of these structures can be unsubstituted or substituted with one or more R groups, each R is independently H, $C_1$-$C_{10}$ alkyl, $C_2$-$C_{10}$ alkenyl, $C_2$-$C_{10}$ alkynyl, hydroxy $C_1$-$C_{10}$ alkyl, $C_1$-$C_{10}$ alkoxy, halogenated $C_1$-$C_{20}$ alkyl, halogen, —OH, —NO$_2$, —CN, —COOH, —CHO, —SO$_3$H, —SO$_2$R, —SOR, —NH$_2$, —NHR, —NR$_2$, —CHal$_3$, —NHCO($C_1$-$C_{10}$)alkyl, —CONHR, —C(O)R, —CO$_2$R, —C(O)N(R)$_2$, —NRC(O)R, —NRC(O)N(R)$_2$, —NRSO$_2$R; a 3-8 membered saturated or partially unsaturated cycloalkyl, $C_{3-10}$ aryl, a 3-7 membered heterocylic ring having 1-4 heteroatoms that are independently selected from nitrogen, oxygen, or sulfur, or a 5-6 membered heteroaryl having 1-4 heteroatoms that are independently selected from nitrogen, oxygen, or sulfur;

or a stereoisomeric form or a mixture of stereoisomeric forms, or pharmaceutically acceptable salts thereof.

In some embodiments of the TLR9 inhibitor, for the formula I-III, T is T5 with Z being 0 and X represents (—$CH_2$—)$_n$ wherein n=1 to 24, thereby forming an alkylene chain, wherein the alkylene chain is optionally substituted with halogen, $C_1$-$C_{20}$ alkyl, $C_2$-$C_{10}$ alkenyl, $C_2$-$C_{10}$ alkynyl, halogenated $C_1$-$C_{10}$ alkyl, hydroxy $C_1$-$C_{10}$ alkyl, or $C_1$-$C_{10}$alkoxy.

Further, the invention relates to a compound of formula (III) as defined herein, wherein one of W, U, E and J represents —CH(T)- or N-T and the rest of W, U, E and J are independently absent or independently represent $CH_2$, $CR_2$, NR or S; and T represents:

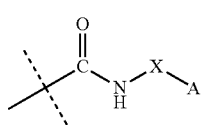
(T1)

wherein X is —($CH_2$)$_n$— and n is 1 to 5,

A is 3-8 membered substituted or unsubstituted cycloalkyl, heterocyclyl, aryl or heteroaryl, or A is 3 to 8 membered heterocyclyl fused with an aryl or heteroaryl, which can be unsubstituted or substituted with one or more R substituents; or a stereoisomeric form or a mixture of stereoisomeric forms, or pharmaceutically acceptable salts thereof.

In yet another aspect of the present invention, in the formula (III), one of W, U, E and J represents —CH(T)- or N-T and the rest of W, U, E and J are independently absent or independently represent $CH_2$, $CR_2$, NR or S; T represents:

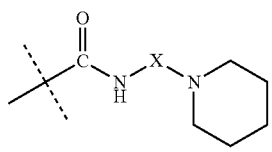
(T4)

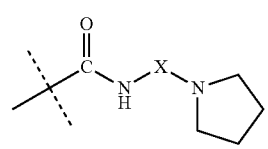
(T5)

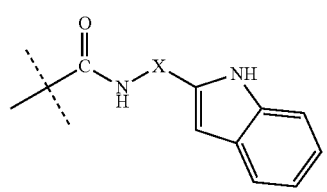
(T6)

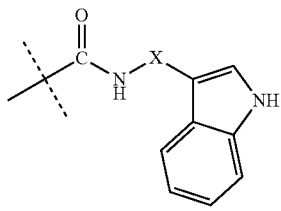
(T7)

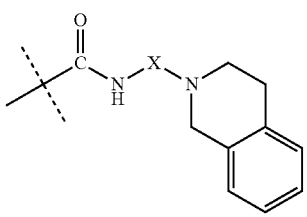
(T8)

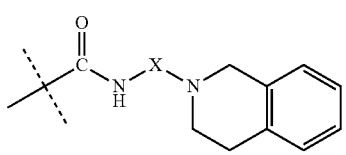
(T9)

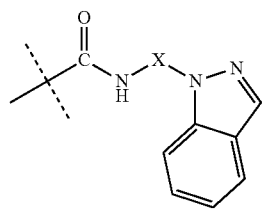
T10

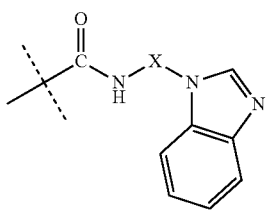
T11

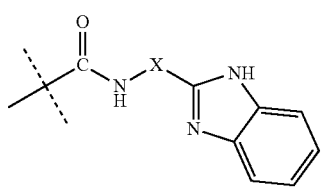
T12

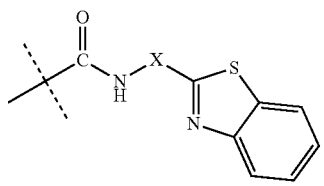
T13 wherein the rings in T4, T5, T6, T7, T8, T9, T10, T11, or T12 are unsubstituted or substituted with one or more R groups, wherein each R is independently H, C1-C10 alkyl, C2-C10 alkenyl, C2-C10 alkynyl, hydroxy $C_1$-$C_{10}$ alkyl, $C_1$-$C_{10}$ alkoxy, halogenated $C_1$-$C_{20}$ alkyl, halogen, —OH, —$NO_2$, —CN, —COOH, —CHO, —$SO_3H$, —$SO_2R$, —SOR, —$NH_2$, —NHR, —$NR_2$, —$CHal_3$, —NHCO($C_1$-$C_{10}$)alkyl, —CONHR, —C(O)R, —$CO_2R$, —C(O)N(R)$_2$, —NRC(O)R, —NRC(O)N(R)$_2$, —$NRSO_2R$; a 3-8 membered saturated or partially unsaturated cycloalkyl, $C_{3-10}$ aryl, a 3-7 membered heterocylic ring having 1-4 heteroatoms that are independently selected from nitrogen, oxygen, or sulfur, or a 5-6 membered heteroaryl having 1-4 heteroatoms that are independently selected from nitrogen, oxygen, or sulfur; or a stereoisomeric form or a mixture of stereoisomeric forms, or pharmaceutically acceptable salts thereof.

Further the invention relates to a compound of formula (III) as defined herein, wherein one of W, U, E and J represents —CH(T)- or N-T and the rest of W, U, E and J are independently absent or independently represent $CH_2$, $CR_2$, NR or S; X in the T structures represents $(—CH_2—)_n$ wherein n=1 to 6, thereby forming an alkylene chain, wherein the carbon atoms of the alkylene chain can be replaced by at least one heteroatom, wherein the heteroatoms are independently —O—, or —NH—, with the proviso that each heteroatom is separated from each other heteroatom by at least one carbon atom; the alkylene chain is optionally substituted with a halogen, $C_1$-$C_6$ alkyl, $C_2$-$C_8$ alkenyl, $C_3$-$C_8$ cycloalkyl, $C_2$-$C_8$ alkynyl, halogenated $C_1$-$C_6$ alkyl, hydroxy $C_1$-$C_6$alkyl, or $C_1$-$C_6$ alkoxy;
A represents a fragment or structure selected from:

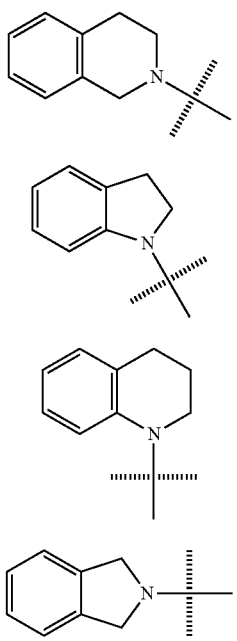

in which the structures for A can be unsubstituted or substituted with one or more R groups that are independently selected from $C_1$-$C_6$ alkyl, —F, —Cl, —CHF$_2$, —CF$_3$, —OMe, —OEt, hydroxy $C_1$-$C_4$ alkyl, —OH, or —CN; or a stereoisomeric form or a mixture of stereoisomeric forms, or pharmaceutically acceptable salts thereof.

In yet another aspect of the present invention, in the compound of formula (III) as defined herein, the $R_1$ and $R_2$ are independently selected from halogen, —CN, $C_1$-$C_{10}$ alkoxy (—OC$_1$-$C_{10}$alkyl), —CHal$_3$, —C(O)OR, wherein R is H, $C_1$-$C_{10}$ alkyl, NR$_2$, wherein R is independently H or $C_1$-$C_{10}$ alkyl, or two R groups together can form a 3-8 membered saturated or unsaturated carbocyclic or heterocyclic ring which contains at least one heteroatom selected from N, S and O,
or a stereoisomeric form or a mixture of stereoisomeric forms, or pharmaceutically acceptable salts thereof.

In yet another aspect, in the formula (III) as defined herein, wherein A represents:

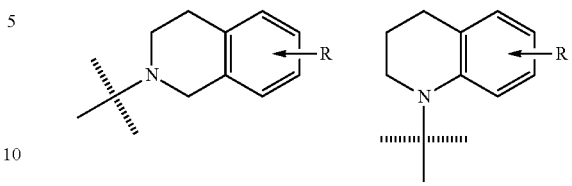

wherein the number of R groups is varied from 1 to 3, and each R is independently selected from halogen, $C_1$-$C_6$ alkyl, $C_2$-$C_8$ alkenyl, $C_3$-$C_8$ cycloalkyl, $C_2$-$C_8$ alkynyl, halogenated $C_1$-$C_6$ alkyl, hydroxy $C_1$-$C_6$ alkyl, or $C_1$-$C_6$ alkoxy, or a stereoisomeric form or a mixture of stereoisomeric forms, or pharmaceutically acceptable salts thereof.

In yet another aspect of the present invention, the compound is a compound of formula (IV):

(Formula IV)

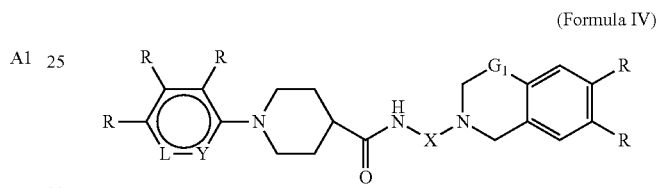

wherein,
Y and L are independently CH or N; or optionally one of Y and L is absent,
G1 is $CH_2$ or absent,
each R is independently selected from H, halogen, $C_1$-$C_6$ alkyl, $C_3$-$C_8$ cycloalkyl, halogenated $C_1$-$C_6$ alkyl, hydroxy $C_1$-$C_6$ alkyl, $C_1$-$C_6$alkoxy, or —CN;
X represents $(—CH_2—)_n$ wherein n=1 to 6, thereby forming an alkylene chain, the alkylene chain is optionally substituted with halogen, $C_1$-$C_6$ alkyl, $C_2$-$C_8$ alkenyl, $C_3$-$C_8$ cycloalkyl, $C_2$-$C_8$ alkynyl, halogenated $C_1$-$C_6$alkyl, hydroxy $C_1$-$C_6$ alkyl, or $C_1$-$C_6$ alkoxy;
or a stereoisomeric form or a mixture of stereoisomeric forms, or pharmaceutically acceptable salts thereof.

In some embodiments, the TLR9 inhibitor of Formula IV can include: Y and L are independently CR or CH, G1 is $CH_2$ or absent, each R is independently selected from H, halogen, halogenated $C_1$-$C_6$ alkyl, hydroxy $C_1$-$C_6$ alkyl, $C_1$-$C_6$alkoxy, or —CN, X represents $(—CH_2—)_n$ wherein n=1 to 6, thereby forming an alkylene chain, or a stereoisomeric form or a mixture of stereoisomeric forms, or pharmaceutically acceptable salts thereof.

In yet another aspect of the present invention, the compound is a compound of formula (V):

(Formula V)

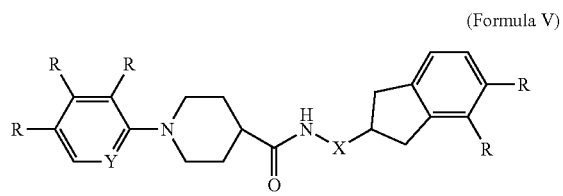

wherein
Y is CH or N; or Y is absent,
each R is independently selected from H, halogen, $C_1$-$C_6$ alkyl, $C_3$-$C_8$ cycloalkyl, halogenated $C_1$-$C_6$ alkyl, hydroxy $C_1$-$C_6$ alkyl, $C_1$-$C_6$alkoxy, or —CN;
X represents (—$CH_2$—)$_n$ wherein n=1 to 6, thereby forming an alkylene chain, the alkylene chain is optionally substituted with halogen, $C_1$-$C_6$ alkyl, $C_2$-$C_8$ alkenyl, $C_3$-$C_8$ cycloalkyl, $C_2$-$C_8$ alkynyl, halogenated $C_1$-$C_6$ alkyl, hydroxy $C_1$-$C_6$ alkyl, or $C_1$-$C_6$alkoxy;
or a stereoisomeric form or a mixture of stereoisomeric forms, or pharmaceutically acceptable salts thereof.

In some embodiments, the TLR9 inhibitor can include a compound of formula (VI):

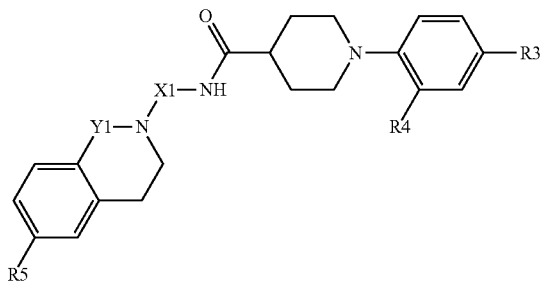

(Formula VI)

wherein: $Y^1$ is CH or absent; $X^1$ represents (—$CH_2$—)$_n$ wherein n=1 to 4, thereby forming an alkylene chain, the alkylene chain is optionally substituted with halogen, $C_1$-$C_6$ alkyl, $C_2$-$C_8$ alkenyl, $C_3$-$C_8$ cycloalkyl, $C_2$-$C_8$ alkynyl, halogenated $C_1$-$C_6$ alkyl, hydroxy $C_1$-$C_6$ alkyl, or $C_1$-$C_6$alkoxy; $R^3$ is one or more of, independently of each other, H, halogen, halogenated $C_1$-$C_{10}$ alkyl, hydroxy $C_1$-$C_{10}$ alkyl, $C_1$-$C_{10}$ alkoxy, or —CN; $R^4$ is one or more of, independently of each other, H, halogen, halogenated $C_1$-$C_{10}$ alkyl, hydroxy $C_1$-$C_{10}$ alkyl, $C_1$-$C_{10}$ alkoxy, or —CN; or a stereoisomeric form or a mixture of stereoisomeric forms, or pharmaceutically acceptable salts thereof.

In some embodiments of formula (VI), $Y^1$ is CH or absent; $X^1$ represents (—$CH_2$—)$_n$ wherein n=2 or 3, thereby forming an alkylene chain; $R^3$ is one or more of, independently of each other, H, halogen, or —CN; $R^4$ is one or more of, independently of each other, H, halogen, halogenated $C_1$-$C_{10}$ alkyl; or a stereoisomeric form or a mixture of stereoisomeric forms, or pharmaceutically acceptable salts thereof.

In some embodiments of formula (VI), $Y^1$ is CH or absent; $X^1$ represents (—$CH_2$—)$_n$ wherein n=2 or 3, thereby forming an alkylene chain; $R^3$ is —CN; $R^4$ is H or halogen; or a stereoisomeric form or a mixture of stereoisomeric forms, or pharmaceutically acceptable salts thereof.

In some embodiments of formula (VI), $Y^1$ is CH; $X^1$ represents (—$CH_2$—)$_n$ wherein n=2 or 3, thereby forming an alkylene chain; $R^3$ is —CN; $R^4$ is H or halogen; or a stereoisomeric form or a mixture of stereoisomeric forms, or pharmaceutically acceptable salts thereof.

Further the terms as used herein are defined.

The term "alkyl", as used herein, means a straight-chain (i.e., unbranched) or branched hydrocarbon chain that is completely saturated. Alkyl groups contain 1-12 carbon atoms. In some embodiments, alkyl groups contain 1-6 carbon atoms. In other embodiments, aliphatic groups contain 1-4 aliphatic carbon atoms. In still other embodiments, alkyl groups contain 1-3 carbon atoms, and in yet other embodiments, aliphatic groups contain 1-2 aliphatic carbon atoms.

Exemplary alkyl groups are methyl, ethyl, propyl, isopropyl, butyl, isobutyl, tert-butyl, pentyl, hexyl, heptyl, nonyl and decyl.

The term "cycloalkyl", as used herein, refers to a monocyclic $C_3$-$C_8$ hydrocarbon that is completely saturated or that contains one or more units of unsaturation, but which is not aromatic, that has a single point of attachment to the rest of the molecule. Exemplary groups include cyclopropyl, cyclobutyl, cyclopentyl, cyclohexyl, cycloheptyl, cycooctyl, cyclodecyl, cyclododecyl and adamantyl.

Unless otherwise indicated, the term "alkenyl" as used herein by itself or as part of another group refers to straight or branched chain radicals of 2 to 20 carbons, in some embodiments 2 to 12 carbons, and in some embodiments 2 to 8 carbons in the main chain, which include one or more double bonds in the main chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like. "Substituted alkenyl" includes an alkenyl group optionally substituted with one or more substituents, such as the substituents included above in the definition of "alkyl" and "cycloalkyl".

Unless otherwise indicated, the term "alkynyl" as used herein by itself or as part of another group refers to straight or branched chain radicals of 2 to 20 carbons, in some embodiments 2 to 12 carbons and in some embodiments 2 to 8 carbons in the normal chain, which include one or more triple bonds in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like. "Substituted alkynyl" includes an alkynyl group optionally substituted with one or more substituents, such as the substituents included above in the definition of "alkyl" and "cycloalkyl."

The term "halogen" means F, Cl, Br, or I.

The terms "halogenated alkyl", "halogenated alkenyl" and "alkynyl" as used herein alone or as part of another group refers to "alkyl", "alkenyl" and "alkynyl" which are substituted by one or more atoms selected from fluorine, chlorine, bromine, fluorine, and iodine.

The term "alkoxyl" refers to straight and branched aliphatic hydrocarbon chains attached to an oxygen atom, for example methoxy, ethoxy, n-propoxy, isopropoxy and the like.

The term "heteroatom" means one or more of oxygen, sulfur, nitrogen, or phosphorus (including, any oxidized form of nitrogen, sulfur, or phosphorus; the quaternized form of any basic nitrogen or; a substitutable nitrogen of a heterocyclic ring, for example N (as in 3,4-dihydro-2H-pyrrolyl), NH (as in pyrrolidinyl) or NR+ (as in N-substituted pyrrolidinyl)).

The term "alkylene" refers to a bivalent alkyl group. An "alkylene chain" is a polymethylene group, i.e., —(CH2)n-, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

The term "aryl" used individually or as part of a larger moiety as in "aralkyl", "aralkoxy", or "aryloxy alkyl", unless otherwise indicated, refers to monocyclic and bicyclic ring systems having a total of 3 to 14 ring members, wherein at least one ring in the system is aromatic and wherein each ring in the system contains three to seven ring members. In certain embodiments of the present invention, "aryl" refers to an aromatic ring system. Exemplary aryl groups are cyclopentadienyl, phenyl, biphenyl, naphthyl, anthracyl and the like. Also included within the scope of the term "aryl", as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" used alone or as part of a larger moiety, e.g., "heteroaralkyl", or "heteroaralkoxy", refer to groups having 5 to 10 ring atoms, preferably 5, 6, or 9 ring atoms; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen.

Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl, indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one.

The term "heteroaralkyl" refers to an alkyl group substituted by a heteroaryl, bonded with alkyl and heteroaryl portions.

The term "heterocyclyl", unless otherwise indicated, refers to a 3- to 7-membered, preferably 5- to 7-membered, monocyclic or 7-10-membered bicyclic heterocyclic moiety which can be saturated or partially unsaturated. In addition to carbon atoms, one or more, preferably one to four, heteroatoms, can be contained as defined above.

Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. Also within the invention heterocyclyl ring can be fused to one or more aryl, heteroaryl, or cycloalkyl rings, such as indolinyl, 3H-indolyl, chromanyl, phenanthridinyl, or tetrahydroquinolinyl, where the radical or point of attachment is on the heterocyclyl ring. A heterocyclyl group is optionally mono- or bicyclic.

When forming a radical, a heterocyclic ring can be attached to the main molecule at any heteroatom or carbon atom that allow to form a stable structure.

The term "monocyclic" refers to a monovalent saturated or partially unsaturated or aromatic cyclic radical having no fused rings attached, but optionally having substituents in any suitable atom within the cycle.

Unless otherwise indicated, an "optionally substituted" group has a suitable substituent at any moiety position available for substitution. Number of substituent is defined by stability of molecule and while choosing the substituents the one skilled in the art would easily define which character and number of substituents can be used depending on the application field. If otherwise indicated, the substituent can be selected from H, $C_1$-$C_{20}$ alkyl, $C_2$-$C_{20}$ alkenyl, $C_2$-$C_{20}$ alkynyl, halogenated $C_1$-$C_{20}$ alkyl, halogen, —OH, —NO$_2$, —CN, —COOH, —CHO, —SO$_3$H, —SO$_2$R, —SOR, —NH$_2$, —NHR, —NR$_2$, —CHal$_3$, —NHCO($C_1$-$C_{10}$)alkyl, —CONHR, —C(O)R, —CO$_2$R, —C(O)N(R)$_2$, —NRC(O) R, —NRC(O)N(R)$_2$, —NRSO$_2$R; a 3-8 membered saturated or partially unsaturated cycloalkyl, $C_{3-10}$ aryl, a 3-7 membered heterocylic ring having 1-4 heteroatoms independently selected from nitrogen, oxygen, or sulfur, or a 5-6 membered heteroaryl having 1-4 heteroatoms independently selected from nitrogen, oxygen, or sulfur.

As used herein, the term "pharmaceutically acceptable salt" refers to those salts which are suitable to use within mammals and do not tend to be toxic. Pharmaceutically acceptable salts are formed using inorganic and organic acids and bases. Examples of pharmaceutically acceptable salts are salts of an amino group formed with inorganic acids such as hydrochloric acid, hydrobromic acid, phosphoric acid, sulfuric acid and perchloric acid, or with organic acids such as tartaric acid, acetic acid, oxalic acid, maleic acid, citric acid, succinic acid or malonic acid, terephthalic acid. Other pharmaceutically acceptable salts include adipate, ascorbate, aspartate, benzoate, bisulfate, borate, butyrate, valerate, camphorate, camphorsulfonate, cyclopentanepropionate, formate, citrate, oxalate, pivalate, succinate, tartrate, fumarate, gluconate, hemisulfate, heptanoate, hexanoate, hydroiodide, 2-hydroxy-ethanesulfonate, lactate, laurate, lauryl sulfate, maleate, malonate, methanesulfonate, 2-naphthalenesulfonate, nicotinate, nitrate, oleate, palmitate, stearate, undecanoate, alginate, 3-phenylpropionate, phosphate, sulfate, thiocyanate, p-toluenesulfonate, benzenesulfonate, persulfate, ethanesulfonate, dodecylsulfate, and the like and mixture salts.

Salts derived from appropriate bases include alkali metal, alkaline earth metal, ammonium and N(Calkyl) salts. Representative alkali or alkaline earth metal salts include Sodium, lithium, potassium, calcium, magnesium, and the like. Further pharmaceutically acceptable salts include, when appropriate, nontoxic ammonium, quaternary ammonium, and amine cations formed using counterions, such as halide, hydroxide, carboxylate, sulfate, phosphate, nitrate, alkyl sulfonate and aryl sulfonate.

The compounds of the Formulae I-VI include all possible optical isomers and racemic mixtures thereof. Unless otherwise stated, structures depicted herein are meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereo chemical isomers as well as enantiomeric, diastereomeric, and geometric (or conformational) mixtures of the present compounds are within the scope of the invention. Unless otherwise stated, all tautomeric forms of the compounds of the invention are within the scope of the invention.

The compounds of Formulae I-VI can be used in the form of addition salts. More particular, acid addition salts can be used such as chlorides, nitrates, sulfates, phosphates, methane sulfonates and salts of other pharmaceutically acceptable acids. Pharmaceutically acceptable acid-addition salts of compounds of Formula I are generally prepared by reaction of the respective compound with an equimolar amount of a relatively strong acid, preferably an inorganic acid such as hydrochloric, sulfuric or phosphoric acid or an organic acid such as methanesulfonic acid in a polar solvent. Isolation of the salt is facilitated by the addition of a solvent in which the salt is insoluble, an example of such a solvent being diethyl ether.

In yet another aspect of the present invention, a pharmaceutical composition is provides comprising one or more compounds as indicated above or a salt thereof and a pharmaceutically acceptable carrier or diluent. More particularly, the pharmaceutical composition according is useful in the treatment of a disorder or disease which is mediated by the activity of TLR9, autoimmune diseases and/or inflammatory diseases and/or cancer. The disorders can be selected from hypersensitivity, diseases associated with the over-stimulation of host's (subject or patient) immune system by microbes, interferon-mediated diseases or inflammatory cytokine-mediated inflammation diseases.

In another aspect of the present invention, the compound of the invention is capable of inhibiting TLR9 specifically or preferentially over other TLRs. For example, the compounds can inhibit TLR9 over TLR7 and TLR8.

In another aspect of the present invention claimed is a pharmaceutical composition comprising one or more compounds of formulae I to VI and specific embodiments below, or a salt thereof; and a pharmaceutically acceptable carrier or diluent.

In another aspect of the present invention claimed is a pharmaceutical composition for use in the treatment of a disorder or disease which is mediated by the activity of TLR9, such as autoimmune diseases and/or inflammatory diseases and/or cancer.

The disorders are selected from diseases associated with the over-stimulation of host's immune system by microbes, interferon-mediated diseases or inflammatory cytokine-mediated inflammation diseases. Preferably the disorder is selected from antiphospholipid syndrome, autoimmune hepatitis, autoimmune myocarditis, autoimmune orchitis, autoimmune pancreatitis, autoimmune retinopathy, rheumatoid arthritis, psoriatic arthritis, osteoarthritis, systemic Lupus Erythematosus, lupus nephritis, osteoporosis, systemic sclerosis, multiple sclerosis, psoriasis, diabetes, inflammatory bowel disease (Crohn's Disease and Ulcerative Colitis), Hyperimmunoglobulinemia D, periodic fever syndrome, systemic juvenile idiopathic arthritis, sepsis, atherosclerosis, Celiac disease, Sjogren's Syndrome, Alzheimer's disease, Parkinson's disease, and cancer.

Preferably, cancer is selected from colorectal cancer, breast cancer, ovarian carcinoma, pancreatic cancer, lung cancer, renal cell carcinoma, cervical cancer and multiple myeloma.

In another aspect, a method is claimed for inhibiting TLR9 activity in a subject comprising the step of administering to said subject with a compound according to the present invention or a pharmaceutically acceptable salt thereof.

The method comprises contacting cells which express the TLR9 in an amount that is sufficient to inhibit the TLR9. The method can be practiced in vivo or in vitro.

In another embodiment, the invention relates to a method of treating a condition in a patient that is mediated by the binding of TLR9. The method comprises administering to the subject a therapeutically effective amount of a compound of the invention. Preferably, the compound to be administered selectively inhibits the TLR9.

The amount of compound in compositions of this invention is such that it is effective to measurably inhibit TLR9 in a subject.

The term "subject", as used herein, means an animal, preferably a cell, biological tissue, or animal, preferably mammal, and most preferably a human.

The term "pharmaceutically acceptable carrier or pharmaceutically acceptable vehicle" refers to a non-toxic carrier, adjuvant, or vehicle that does not substantially vary the pharmacological activity of the compound with which it is formulated. Pharmaceutically acceptable carriers or vehicles that are used in the compositions of this invention include, but are not limited to, lecithin, glycine, sorbic acid, potassium sorbate, sodium chloride, zinc salts, colloidal silica, magnesium trisilicate, polyvinyl pyrrolidone, cellulose-based substances, polyethylene glycol, buffer substances such as cytric acid and phosphates, A method of the present invention treats disorders are selected from diseases associated with the over-stimulation of host's immune system by microbes, interferon-mediated diseases or inflammatory cytokine-mediated inflammation diseases. Preferably, the disease is selected from antiphospholipid syndrome, autoimmune hepatitis, autoimmune myocarditis, autoimmune orchitis, autoimmune pancreatitis, autoimmune retinopathy, rheumatoid arthritis, psoriatic arthritis, osteoarthritis, systemic Lupus Erythematosus, lupus nephritis, osteoporosis, systemic sclerosis, multiple sclerosis, psoriasis, diabetes, inflammatory bowel disease (Crohn's Disease and Ulcerative Colitis), Hyperimmunoglobulinemia D, periodic fever syndrome, systemic juvenile idiopathic arthritis, sepsis, atherosclerosis, Celiac disease, Sjogren's Syndrome, Alzheimer's disease, Parkinson's disease, and cancer, preferably selected from colorectal cancer, breast cancer, ovarian carcinoma, pancreatic cancer, lung cancer, renal cell carcinoma, cervical cancer and multiple myeloma.

Compositions of the present invention comprising the compounds of Formulae (I) to (VI) and specific compounds below described as TLR9 inhibitors of the present invention and optionally at least one pharmaceutically acceptable carrier, are acceptable for any administration. In particular, they can be administered orally, parenterally, by inhalation spray, topically, rectally, nasally, buccally, vaginally or via an implanted reservoir.

The term "parenteral" as used herein includes subcutaneous, intravenous, intramuscular, etc. Preferably, the compositions are to be administered orally, or intravenously. Among the acceptable vehicles and solvents that are employed are water and Ringer's solution, alone or in combination with mono- or di- or poly-glycerides.

Pharmaceutically acceptable compositions of this invention are orally administered in any orally acceptable dosage form. Exemplary oral dosage forms are capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch.

Pharmaceutically acceptable compositions of this invention comprising the compounds of Formulae (I) to (VI) described as TLR9 inhibitors of the present invention are also administered topically, especially when the target of treatment includes areas or organs readily accessible by topical application, including diseases of the eye, the skin, or the lower intestinal tract. Suitable topical formulations are readily prepared for each of these areas or organs.

For topical applications, provided pharmaceutically acceptable compositions are formulated in a suitable ointment wherein the compound of the invention, optionally with other active components, is suspended or dissolved in one or more carriers. Exemplary carriers for topical administration of compounds of this are mineral oil, propylene glycol, polyoxyethylene and water. Suitable topical carriers include, but are not limited to, mineral oil, sorbitan monostearate, polysorbates, cetyl alcohol, benzyl alcohol and water.

Pharmaceutically acceptable compositions of this invention are optionally administered by nasal aerosol or inhalation. Such compositions are prepared according to techniques well-known in the art of pharmaceutical formulation and are prepared as solutions in saline, employing certain conservants, including benzyl alcohol or other suitable preservatives, and/or other conventional solubilizing or dispersing agents.

The amount of the compounds of Formulae (I) to (VI) described as TLR9 inhibitors of the present invention of the present invention that are optionally combined with the carrier of vehicle materials to produce a composition in a single dosage form for treating a subject will vary depending upon the host treated, the particular mode of administration. Preferably, provided compositions should be formulated so that a dosage of between 0.01-100 mg/kg body weight/day of the compound can be administered to a patient receiving these compositions.

The compounds of Formulae (I) to (VI) described as TLR9 inhibitors of the present invention can also be in micro-encapsulated form with one or more excipients as noted above. The solid dosage forms of tablets, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms also comprise, as is normal practice, additional substances other than inert diluents, e.g., tableting lubricants and other tableting aids such a magnesium stearate and microcrystalline cellulose. In the case of capsules, tablets and pills, the dosage forms optionally also comprise buffering agents. They optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

The compounds of Formulae (I) to (VI) described as TLR inhibitors of the present invention can may be useful as a within a pharmaceutical composition as a vaccine adjuvant for use in conjunction with any material that modulates immune response, such as, for example, live viral, bacterial, or parasitic immunogens; inactivated viral, tumor-derived, protozoal, organism-derived, fungal, or bacterial immunogens, toxoids, toxins; self-antigens; polysaccharides; proteins; glycoproteins; peptides; cellular vaccines; DNA vaccines; recombinant proteins; glycoproteins; peptides; and the like. In some aspects, the combination therapy including but not limited to the combination of a TLR9 inhibitor and a vaccine is used in the treatment of an autoimmune disease or an inflammatory disorder. In some aspects, the combination therapy including but not limited to the combination of a TLR9 inhibitor and a vaccine is used in the treatment of an infectious disease.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The present invention furthermore relates to a method for treating a subject suffering from a TLR9 related disorder, comprising administering to said subject an effective amount of a compound of formulae (I) to (VI), in a therapeutically effective amount.

The term "therapeutically effective amount", as used herein, refers to a dosage and duration of administration which is commonly known in the art and recognized and utilized by the medical community. Such an amount will vary depending on the particular agent(s) administered, the size and/or condition of the subject receiving treatment or other medical factors determined by the administering physician.

The compounds of the present invention are useful as anticancer agents for cancers that are responsive to TLR9 activation. In certain embodiments, the cancers include, but are not limited to cancer of the breast, bladder, bone, brain, central and peripheral nervous system, colon, sarcoma, ovary, pancreas, prostate, rectum, renal, small intestine, soft tissue, testis, stomach, skin, ureter, vagina and vulva; inherited cancers, retinomblastoma, Wilms tumor, leukemia, lymphoma, non-Hodgkins disease, chronic and acute myeloid leukaemia, acute lymphoblastic leukemia, Hodgkin's disease, multiple myeloma, and T-cell lymphoma, myelodysplastic syndrome, and AIDS related cancer type diseases.

Immune suppression and/or inhibition according to the methods described herein may be practiced on individuals including those suffering from a disorder associated with an unwanted activation of an immune response. The present disclosure also provides methods for inhibiting a TLR9 induced response (e.g., in vitro or in vivo). In some variations, the cell is contacted with the TLR9 inhibitor in an amount effective to inhibit a response from the cell that contributes to an immune response.

Inhibition of TLR9 can be useful for treating and/or preventing a variety of diseases or disorders associated with cytokine activity. Conditions for which TLR9 inhibitors may be used as treatments include, but are not limited to, autoimmune diseases and inflammatory disorders.

Provided herein are methods of inhibiting an immune response in a subject, the method comprising administering to the individual at least one TLR9 inhibitor as disclosed herein in an amount effective to inhibit the immune response in the individual. In some variations, the immune response is associated with an autoimmune disease. In further aspects, wherein inhibiting the immune response ameliorates one or more symptoms of the autoimmune disease. In still further aspects, wherein inhibiting the immune response treats the autoimmune disease. In yet further aspects, wherein inhibiting the immune response prevents or delays development of the autoimmune disease. In some variations, the TLR inhibitor inhibits a TLR9-dependent immune response. In some aspects, at least one TLR inhibitor is administered in an amount effective to inhibit an immune response in the individual.

Provided herein are also methods of treating or preventing an autoimmune disease in an individual, comprising administering to the individual an effective amount of a TLR9 inhibitor. In some aspects, the autoimmune disease is associated with the skin, muscle tissue, and/or connective tissue. In some embodiments, the autoimmune disease is not evidenced in the individual by skin, muscle tissue, and/or connective tissue symptoms.

In some embodiments, the autoimmune disease is systemic. Autoimmune diseases include, without limitation, rheumatoid arthritis, autoimmune pancreatitis, systemic lupus erythematosus, type I diabetes mellitus, multiple sclerosis, antiphospholipid syndrome, sclerosing cholangitis, systemic onset arthritis, irritable bowel disease, scleroderma, Sjogren's disease, vitiligo, polymyositis, pemphigus vulgaris, pemphigus foliaceus, inflammatory bowel disease including Crohn's disease, ulcerative colitis, and autoimmune hepatitis.

Accordingly, the invention provides a method of inhibiting TLR9 in an animal, especially a mammal, preferably a human comprising administering an effective amount of a compound of Formulae I-VI to the animal. As with all compositions for inhibition of an immune response, the effective amounts and method of administration of the particular TLR9 inhibitor formulation can vary based on the individual, what condition is to be treated and other factors evident to one skilled in the art. An effective amount of a compound will vary according to factors known in the art but is expected to be a dose of about 0.1 to 10 mg/kg, 0.5 to 10 mg/kg, 1 to 10 mg/kg, 0.1 to 20 mg/kg, 0.1 to 20 mg/kg, or 1 to 20 mg/kg.

In some embodiments, the combination therapy including but not limited to the combination of a TLR9 inhibitor and a corticosteroid is used in the treatment of an autoimmune disease or an inflammatory disorder. In some embodiments, the autoimmune disease is selected from but not limited to rheumatoid arthritis, systemic lupus erythematosus, autoimmune skin disease, multiple sclerosis, pancreatitis, glomerulonephritis, pyelitis, Sclerosing cholangitis, and type I diabetes. In some embodiments, the autoimmune disease is Sjogren's disease.

Also provided herein are kits comprising a TLR9 inhibitor as provided herein, and instructions for use in the methods of inhibiting a TLR9-dependent immune response.

The kits may comprise one or more containers comprising a TLR inhibitor (or a formulation comprising a TLR inhibitor) as described herein, and a set of instructions, generally written instructions although electronic storage media (e.g., magnetic diskette or optical disk) containing instructions are also acceptable, relating to the use and dosage of the TLR inhibitor or formulation for the intended treatment (e.g., suppression of a TLR9-dependent immune response, ameliorating one or more symptoms of an autoimmune disease, ameliorating a symptom of chronic inflammatory disease, decreasing cytokine production in response to a virus, and/or treating and/or preventing one or more symptoms of a disease or disorder mediated by TLR9). The instructions included with the kit generally include information as to dosage, dosing schedule, and route of administration for the intended treatment. The containers for the TLR inhibitor (or formulations comprising a TLR inhibitor) may be unit doses, bulk packages (e.g., multi-dose packages) or sub-unit doses. The kits may further comprise a container comprising an adjuvant.

The invention will be further explained with examples which are intended to illustrate the particular embodiments and not to limit the scope of the invention.

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

The symbols and conventions used in the following descriptions of processes, schemes, and examples are consistent with those used in the contemporary scientific literature, for example, the Journal of the American Chemical Society or the Journal of Biological Chemistry. Unless otherwise indicated, all temperatures are expressed in ° C. (degrees Centigrade).

All solvents used were commercially available and were used without further purification. Reactions were typically run using anhydrous solvents. Flash column chromatography was generally carried out using symmetry C18 columns feature trifunctionally bonded C18 ligands on a high purity base-deactived silica.

All NMR spectra were recorded on Bruker DPX-400 NMR spectrometers (400.13 MHz). 1H-NMR chemical shifts ($\delta$H) are quoted in parts per million (ppm) downfield from residual non-deuterated solvent peaks as a reference signal, as per published guidelines (*J. Org. Chem.*, Vol. 62, No. 21, 1997). Abbreviations for NMR data are s (singlet), d (doublet), t (triplet), q (quartet), m (multiplet).

High resolution LC-MS spectra were registered on API 165 EX spectrometer, equipped with Shimadzu LC10 Avp chromatographer and UV-detector Shimadzu SPD 10A vp, light scattering detector ELSD Sedex 75, autosampler Gilson 215.

In general, the compounds of this invention can be prepared from readily available starting materials. If such starting materials are not commercially available, they may be prepared by standard synthetic techniques.

Analytical data of the compounds are summarized in the Table 1 below.

| № | Compound | Physical properties |
|---|---|---|
| 1 | 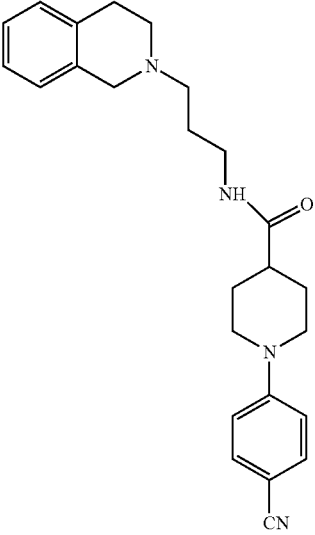 [SMILES: N#Cc1ccc(N2CCC(C(=O)NCCCN3CCc4ccccc4C3)CC2)cc1] | NMR ¹H (DMSO D6): 7.75 (s, 1H), 7.55 (d, 2H), 6.15 (m, 6H), 3.80 (d, 2H), 3.50 (s, 2H), 3.30 (s, 12H), 3.20 (q, 2H), 2.80 (m, 4H), 2.95 (s, 2H), 2.85 (t, 2H), 2.35 (m, 1H), 1.75 (m, 6H).<br>Mass m/z = 403 [M + H]⁺<br>Yield 92%<br>INS020_001 |
| 2 | 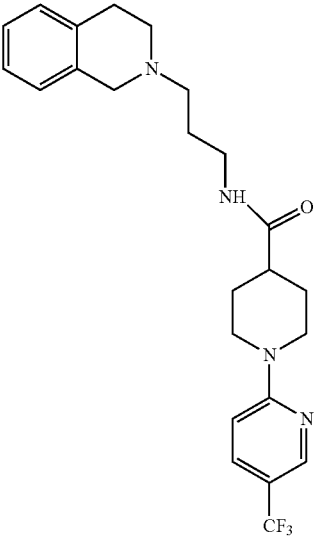 [SMILES: O=C(NCCCN1CCc2ccccc2C1)C1CCN(c2ccc(C(F)(F)F)cn2)CC1] | NMR ¹H (DMSO D6): 8.35 (s, 1H), 7.85 (t, 1H), 7.75 (d, 1H), 7.1 (m, 3H), 6.90 (d, 1H), 4.35 (d, 2H), 3.55 (s, 2H), 3.30 (s, 5H), 3.25 (q, 2H), 2.80 (t, 2H), 2.75 (m, 2H), 2.40-2.55(m, 4H), 1, 52 (m, 4H), 1.45 (q, 2H)<br>Mass m/z = 447 [M + H]⁺<br>Yield 96% |
| 3 | 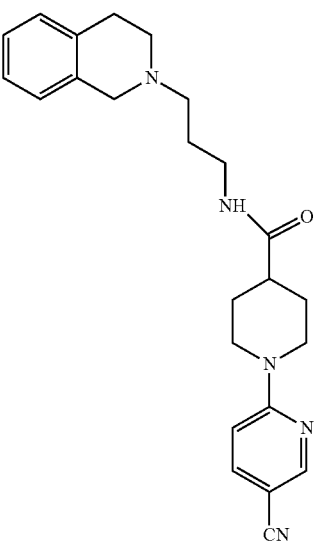 [SMILES: N#Cc1ccc(N2CCC(C(=O)NCCCN3CCc4ccccc4C3)CC2)nc1] | NMR ¹H (DMSO D6): 8.4 (s, 1H), 7.8 (t, 2H), 7, 56 (d, 2H), 6.95-7.2 (m, 4H), 6.85 (d, 1H), 4.40 (d, 2H), 3.95 (s, 2H), 3.30 (s, 4H), 3.20 (q, 2H), 2.85 (t, 2H), 2.60 (m, 2H), 2, 45 (s, 1H), 2.35 (m, 3H), 1.51-1.55 (m, 4H), 1.45 (q, 2H).<br>Mass m/z = 404 [M + H]⁺<br>Yield 95% |

| № | Compound | Physical properties |
|---|---|---|
| 4 | (structure) | NMR ¹H (DMSO D6): 7.8 (s, 1H), 7.55 (d, 2H), 7, 10 (m, 6H), 3.80 (t, 2H), 3.50 (s, 2H), 3.30 (s, 12H), 2.80-3.20 (m, 6H), 2.75 (m, 2H), 2.48 (m, 5H), 2.27 (m, 1H), 1.35-1.80 (m, 6H).<br>Mass m/z = 403 [M + H]⁺<br>Yield 95%<br>INS020_002 |
| 5 | (structure) | Mass m/z = 421 [M + H]⁺<br>Yield 90% |
| 6 | (structure) | NMR ¹H (DMSO D6): 7.80 (s, 1H), 7.60 (d, 2H), 7.00 (m, 6H), 3.90 (d, 2H), 3.55 (s, 2H), 3.30 (m, 10H), 2.60-2.90 (m, 6H), 2.50 (s, 4H), 2.45 (m, 1H), 1.45-1.75 (m, 4H).<br>Mass m/z = 389 [M + H]⁺<br>Yield 91% |

| № | Compound | Physical properties |
|---|---|---|
| 7 | 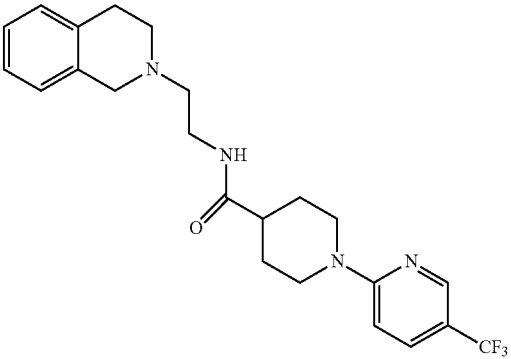 [SMILES: O=C(NCCN1CCc2ccccc2C1)C1CCN(c2ccc(C(F)(F)F)cn2)CC1] | NMR ¹H (DMSO D6): 8.30 (s, 1H), 7.55 (m, 2H), 7.05 (m, 4H), 6.95 (d, 1H), 3.60 (s, 2H), 3.25 (m, 1H), 2.90 (t, 2H), 2.75 (d, 2H), 2.65 (m, 2H), 2.45-2.60 (m, 4H), 1.75 (m, 2H), 1.50 (m, 2H).<br>Mass m/z = 433 [M + H]⁺<br>Yield 93% |
| 8 | 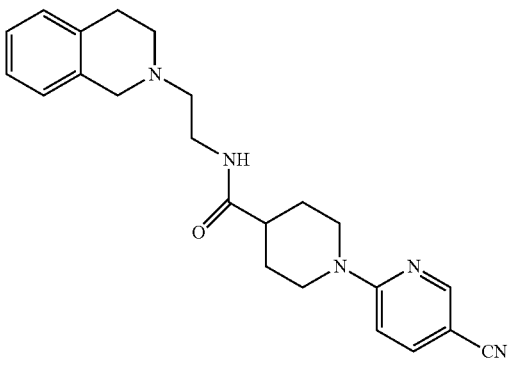 [SMILES: N#Cc1ccc(N2CCC(C(=O)NCCN3CCc4ccccc4C3)CC2)nc1] | NMR ¹H (DMSO D6): 8.45 (s, 1H), 7.60 (m, 2H), 7.20 (m, 4H), 6.80 (d, 2H), 4.80 (d, 2H), 3.25 (m, 2H), 3.22 (t, 6H), 2.80 (t, 2H), 2.75 (m, 2H), 2.65 (m, 2H), 2.50(m, 3H), 1.65 (m, 2H), 1.50 (m, 2H).<br>Mass m/z = 390 [M + H]⁺<br>Yield 93% |
| 9 | 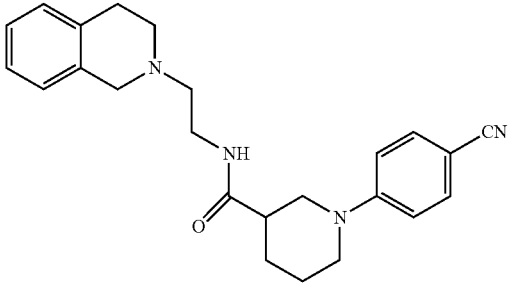 [SMILES: N#Cc1ccc(N2CCCC(C(=O)NCCN3CCc4ccccc4C3)C2)cc1] | Mass m/z = 390 [M + H]⁺<br>Yield 94%<br>INS020_003 |
| 10 | 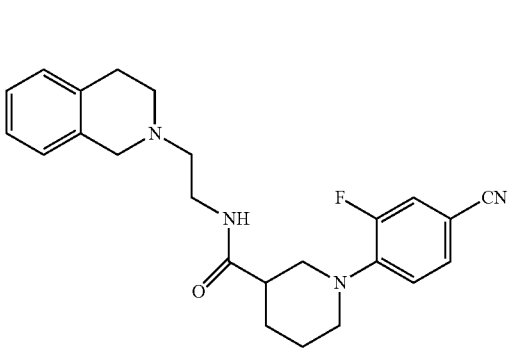 [SMILES: N#Cc1ccc(N2CCCC(C(=O)NCCN3CCc4ccccc4C3)C2)c(F)c1] | NMR ¹H (DMSO D6): 7.85 (s, 1H), 7.65 (d, 1H), 7.48 (m, 1H), 7.10 (m, 4H), 3.60 (m, 4H), 3.30 (m, 6H), 2.85 (t, 1H), 2.65 (m, 2H), 2.55 (m, 4H), 1.75 (m, 2H), 1.55 (m, 2H), 1.45 (m, 1H).<br>Mass m/z = 407 [M + H]⁺<br>Yield 97% |

| № | Compound | Physical properties |
|---|---|---|
| 11 | (structure) | NMR ¹H (DMSO D6): 7.85 (t, 1H), 7.65 (d, 2H), 6.90 (m, 4H), 6.50 (m, 2H), 3.90 (d, 2H), 3.25 (m, 10H), 3.15 (m, 2H), 2.85 (m, 4H), 2.55 (s, 2H), 2.35 (m, 1H), 1.65 (m, 2H), 1.45 (m, 2H).<br>Mass m/z = 375 [M + H]$^+$<br>Yield 91% |
| 12 | (structure) | NMR ¹H (DMSO D6): 8.38 (s, 1H), 7.95 (t, 1H), 7.75 (d, 1H), 6.95 (m, 3H), 6.45 (m, 2H), 4.45 (d, 2H), 3.30 (m, 10H), 3.10 (m, 2H), 2.85 (m, 4H), 2.45 (m, 3H), 2.65 (m, 2H), 1.45 (m, 2H).<br>Mass m/z = 419 [M + H]$^+$<br>Yield 90% |
| 13 | (structure) | NMR ¹H (DMSO D6): 8.45 (s, 1H), 7.95 (m, 1H), 7.77 (d, 1H), 6.90 (m, 2H), 6.50 (m, 2H), 4.45 (d, 2H), 3.25 (m, 12H), 2.80-3.20 (m, 6H), 2.45 (s, 1H), 2.40 (m, 1H), 1.75 (m, 2H), 1.45 (m, 2H).<br>Mass m/z = 376 [M + H]$^+$<br>Yield 92% |

-continued
| № | Compound | Physical properties |
|---|---|---|
| 14 | 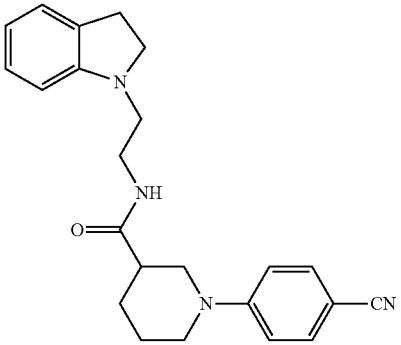 [SMILES: N#Cc1ccc(N2CCCC(C(=O)NCCN3CCc4ccccc43)C2)cc1] | NMR ¹H (DMSO D6): 8.00 (m, 1H), 7.55 (d, 2H), 7.00 (m, 4H), 6.50 (m, 2H), 3.85 (m, 2H), 3.80 (m, 9H), 3.10 (m, 2H), 2.85 (m, 4H), 2.50 (m, 1H), 2.30 (m, 1H), 1.75 (m, 1H), 1.65 (m, 2H), 1.40 (m, 1H).<br>Mass m/z = 375 [M + H]⁺<br>Yield 92% |
| 15 |  | Mass m/z = 393 [M + H]⁺<br>Yield 96%<br>INS020_004 |
| 16 | 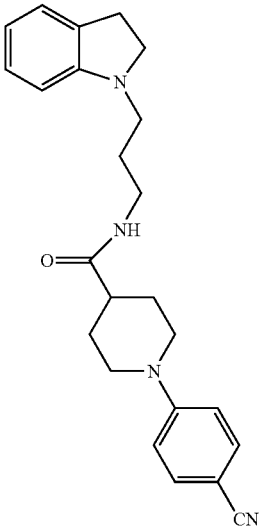 [SMILES: N#Cc1ccc(N2CCC(C(=O)NCCCN3CCc4ccccc43)CC2)cc1] | NMR ¹H (DMSO D6): 7.88 (m, 1H), 7.55 (d, 2H), 6.90 (m, 4H), 6.50 (m, 2H), 4.90 (m, 2H), 3.25 (m, 8H), 3.10 (m, 4H), 2.85 (m, 4H), 2.50 (m, 1H), 2.35 (m, 1H), 1.70 (m, 6H).<br>Mass m/z = 386 [M + H]⁺<br>Yield 98% |

| № | Compound | Physical properties |
|---|---|---|
| 17 | 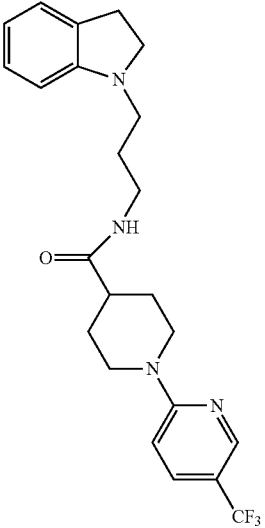 [SMILES: O=C(NCCCN1CCc2ccccc21)C1CCN(c2ccc(C(F)(F)F)cn2)CC1] | NMR $^1$H (DMSO D6): 8.37 (s, 1H), 7.85 (m, 2H), 7.95 (m, 3H), 6.60 (t, 1H), 6.45(m, 1H), 4.45 (d, 2H), 3.25 (m, 6H), 3.10 (m, 2H), 2.85 (m, 6H), 2.45 (m, 2H), 1.65 (m, 4H), 1.45 (m, 2H).<br>Mass m/z = 433 [M + H]$^+$<br>Yield 96% |
| 18 | 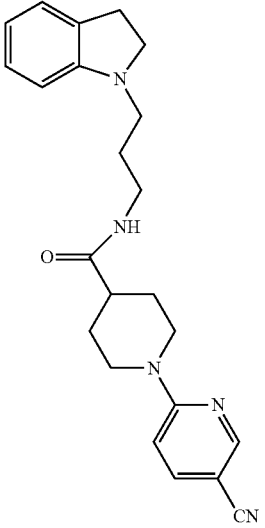 [SMILES: N#Cc1ccc(N2CCC(C(=O)NCCCN3CCc4ccccc43)CC2)nc1] | NMR $^1$H (DMSO D6): 8.45 (s, 1H), 7.90 (t, 1H), 7.75 (m, 1H), 6.95 (m, 3H), 6.45(m, 2H), 3.30 (m, 5H), 3.10 (m, 6H), 2.85 (m, 2H), 2.45 (m, 2H), 1.65 (m, 6H).<br>Mass m/z = 390 [M + H]$^+$<br>Yield 95% |
| 19 | 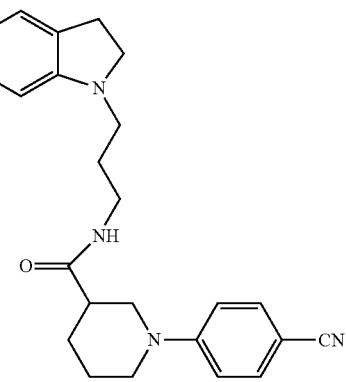 | NMR $^1$H (DMSO D6): 7.95 (s, 1H), 7.55 (d, 2H), 7.95 (m, 4H), 3.95 (t, 2H), 3.80 (m, 8H), 3.30 (m, 5H), 3.20 (m, 2H), 3.00 (m, 3H), 2.85 (m, 2H), 2.55 (s, 1H), 2.35 (m, 1H), 1.90 (m, 1H), 1.79 (m, 4H), 1.45 (m, 1H).<br>Mass m/z = 389 [M + H]$^+$<br>Yield 95% |

-continued
| № | Compound | Physical properties |
|---|---|---|
| 20 | 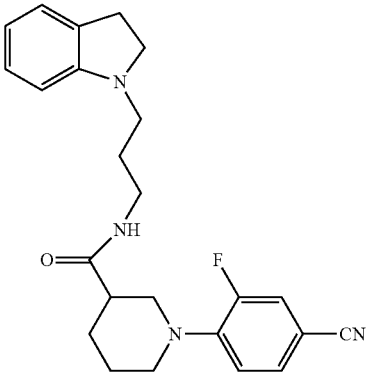 [SMILES: N#Cc1ccc(N2CCCC(C(=O)NCCCN3CCc4ccccc43)C2)c(F)c1] | NMR ¹H (DMSO D6): 7.95 (s, 1H), 7.60 (d, 1H), 7.55 (d, 1H), 7.20 (t, 1H), 6.90 (m, 2H), 6.60 (t, 1H), 6.45 (d, 1H), 3.55 (t, 2H), 3.25 (m, 10H), 3.10 (m, 2H), 2.90 (m, 2H), 2.80 (m, 4H), 1.50-1.80 (m, 6H), 1.45 (m, 1H). Mass m/z = 407 [M + H]⁺ Yield 92% |
| 21 | 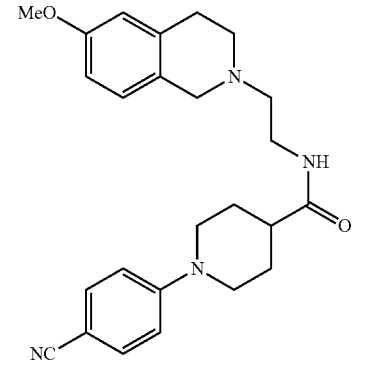 [SMILES: COc1ccc2c(c1)CCN(CCNC(=O)C1CCN(c3ccc(C#N)cc3)CC1)C2] | NMR ¹H (DMSO D6): 7.75 (s, 1H), 7.60 (d, 1H), 6.90 (m, 3H), 6.65 (m, 2H), 3.90 (d, 2H), 3.70 (s, 3H), 3.40 (m, 4H), 3.20 (m, 2H), 2.90 (t, 2H), 2.75 (m, 2H), 2.55 (m, 2H), 2.30 (m, 5H), 1.70 (m, 2H), 1.60 (m, 4H). Mass m/z = 419 [M + H]⁺ Yield 95% |
| 22 | 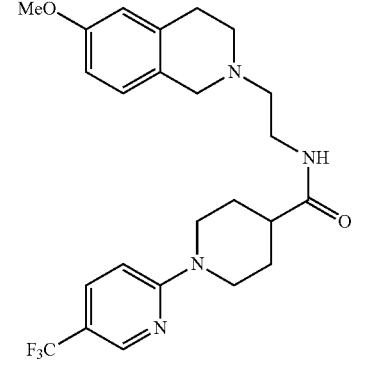 [SMILES: COc1ccc2c(c1)CCN(CCNC(=O)C1CCN(c3ccc(C(F)(F)F)cn3)CC1)C2] | NMR ¹H (DMSO D6): 8.35 (s, 1H), 7 75 (m, 2H), 6.90 (m, 2H), 3.70 (s, 2H), 3.50 (s, 2H), 3.25 (m, 6H), 2.95 (t, 2H), 2.75 (m, 2H), 2.55 (m, 2H), 2.45 (m, 4H), 1.70 (m, 2H), 1.50 (m, 2H). Mass m/z = 463 [M + H]⁺ Yield 93% |
| 23 | 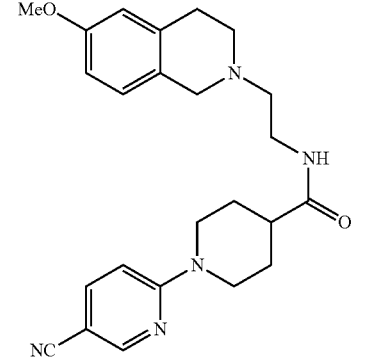 [SMILES: COc1ccc2c(c1)CCN(CCNC(=O)C1CCN(c3ccc(C#N)cn3)CC1)C2] | NMR ¹H (DMSO D6): 8.40 (s, 1H), 7.75 (m, 2H), 6.90 (m, 2H), 6.35 (m, 2H), 4.35 (d, 2H), 3.70 (s, 3H), 3.45 (t, 2H), 3.25 (s, 6H), 2.95 (m, 2H), 2.75 (m, 2H), 2.45 (m, 4H), 1.50 (m, 4H), 1.75 (m, 2H), 1.45 (m, 2H). Mass m/z = 420 [M + H]⁺ |

| № | Compound | Physical properties |
|---|---|---|
| 24 | 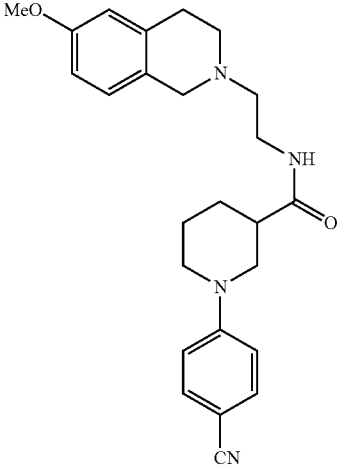 [SMILES: COc1ccc2c(c1)CCN(CCNC(=O)C1CCCN(c3ccc(C#N)cc3)C1)C2] | Mass m/z = 419 [M + H]+<br>Yield 96% |
| 25 | 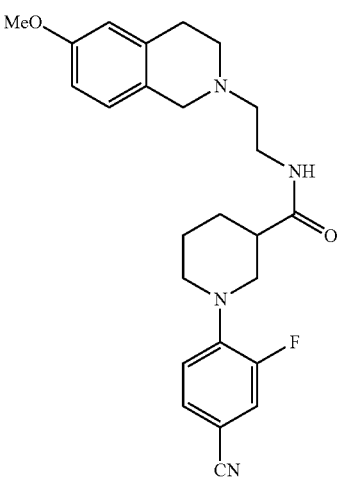 [SMILES: COc1ccc2c(c1)CCN(CCNC(=O)C1CCCN(c3ccc(C#N)cc3F)C1)C2] | Mass m/z = 437 [M + H]+<br>Yield 90%<br>INS020_005 |
| 26 | 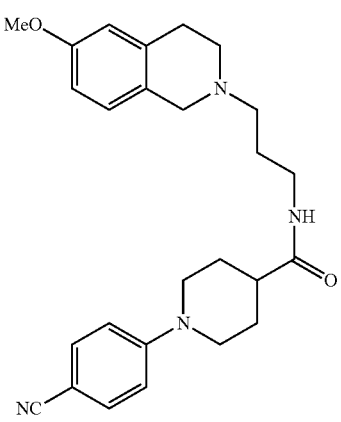 [SMILES: COc1ccc2c(c1)CCN(CCCNC(=O)C1CCN(c3ccc(C#N)cc3)CC1)C2] | NMR ¹H (DMSO D6): 7.80 (t, 1H), 7.60 (d, 2H), 6.95 (m, 32H), 6.65 (m, 2H), 3.85 (d, 2H), 3.65 (s, 3H), 3.10 (q, 2H), 2.90 (t, 2H), 2.70 (m, 2H), 2.60 (m, 2H), 2.50 (m, 2H), 2.40 (m, 2H), 2.30 (m, 2H), 1.60 (m, 6H).<br>Mass m/z = 433 [M + H]+<br>Yield 91% |

| № | Compound | Physical properties |
|---|---|---|
| 27 | 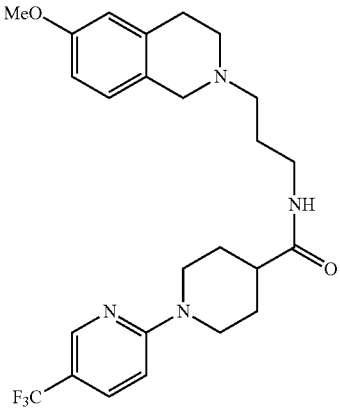 [SMILES: COc1ccc2c(c1)CCN(CCCNC(=O)C1CCN(c3ccc(C(F)(F)F)cn3)CC1)C2] | Mass m/z = 434 [M + H]⁺<br>Yield 95% |
| 28 | 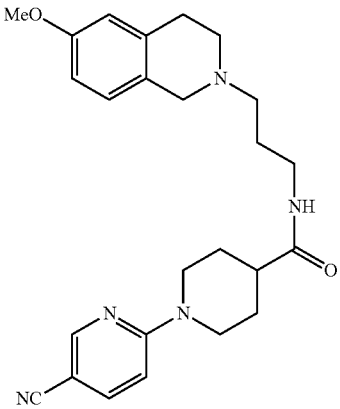 [SMILES: COc1ccc2c(c1)CCN(CCCNC(=O)C1CCN(c3ccc(C#N)cn3)CC1)C2] | NMR ¹H (DMSO D6): 8.40 (s, 1H), 7.80 (m, 2H), 6.80 (t, 2H), 6.60 (m, 2H), 4.40 (d, 2H), 3.70 (s, 3H), 3.40 (s, 1H), 3.30 (s, 4H), 3.10 (q, 2H), 2.90 (t, 2H), 2.78 (m, 2H), 2.65 (m, 2H), 2.50 (m, 1H), 2.30 (m, 2H), 1.60 (m, 6H).<br>Mass m/z = 434 [M + H]⁺<br>Yield 96% |
| 29 | 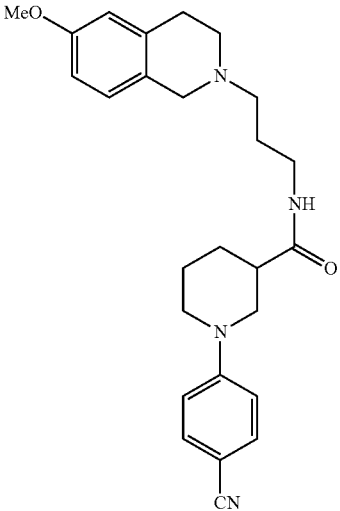 [SMILES: COc1ccc2c(c1)CCN(CCCNC(=O)C1CCCN(c3ccc(C#N)cc3)C1)C2] | NMR ¹H (DMSO D6): 7.90 (s, 1H), 7.45 (d, 2H), 7.25 (s, 1H), 6.90 (m, 1H), 6.70 (d, 2H), 6.65 (m, 1H), 6.60 (s, 1H), 3.55 (m, 7H), 3.45 (m, 2H), 2.75 (m, 8H), 2.45 (m, 1H), 1.75 (m, 3H), 2.65 (m 2H), 2.40 (m, 2H), 1.45 (m, 3H).<br>Mass m/z = 433 [M + H]⁺<br>Yield 97% |

| № | Compound | Physical properties |
|---|---|---|
| 30 | 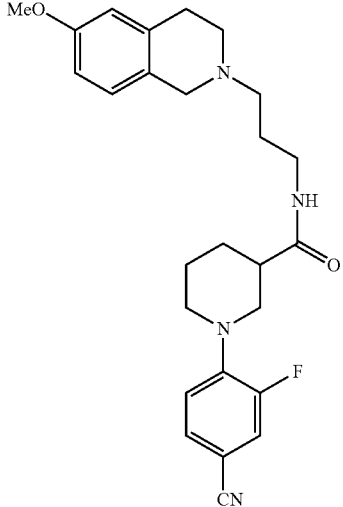 [SMILES: COc1ccc2c(c1)CCN(CCCNC(=O)C1CCCN(c3ccc(C#N)cc3F)C1)C2] | NMR ¹H (DMSO D6): 7.90 (s, 1H), 7.70 (d, 1H), 7.55 (d, 1H), 7.15 (t, 1H), 6.90 (d, 1H), 6.15 (m, 2H), 3.65 (s, 3H), 3.45 (m, 3H), 3.30 (m, 6H), 3.10 (m, 2H), 3.80 (m, 1H), 2.75 (s, 2H), 2.65 (m 2H), 2.40 (m, 2H), 1.65 (m, 6H). Mass m/z = 451 [M + H]⁺ Yield 90% |

In some embodiments, the TLR9 inhibitors are selected from compounds 1, 4, 9, 15, and 25, or from a compound having similar substitution patterns. In some embodiments, the TLR9 inhibitors are selected from only compounds 1, 4, 9, 15, and 25.

In some embodiments, the TLR9 inhibitor is compound 1 (i.e., INS020_001).

In some embodiments, the TLR9 inhibitor is compound 4 (i.e., INS020_002).

In some embodiments, the TLR9 inhibitor is compound 9 (i.e., INS020_003).

In some embodiments, the TLR9 inhibitor is compound 15 (i.e., INS020_004).

In some embodiments, the TLR9 inhibitor is compound 25 (i.e., INS020_005).

Example 1

The compounds of the invention can be prepared using the following procedure.

Compound 1: 1-(4-Cyanophenyl)-N-(3-(3,4-dihydroisoquinolin-2(19)-yl)propyl)piperidine-4-carboxamide

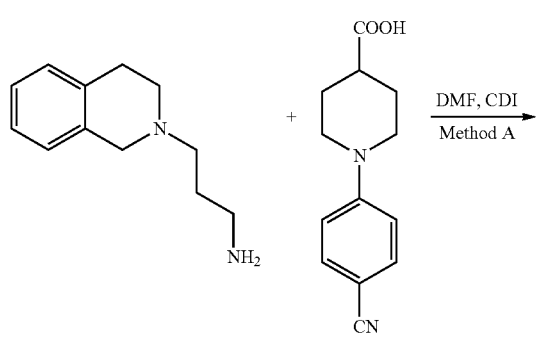

-continued

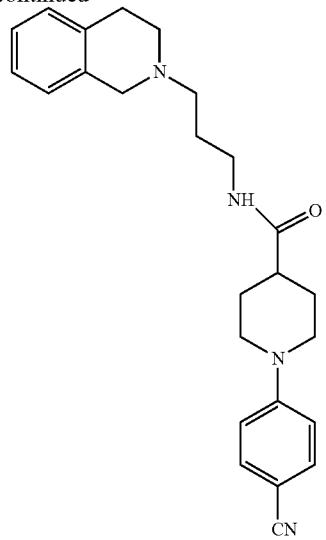

Method A. 1-(4-Cyanophenyl)-N-(3-(3,4-dihydroisoquinolin-2(1H)-yl)propyl)piperidine-4-carboxamide To a solution of 1-(4-cyanophenyl)piperidine-4-carboxylic acid (1 mmol, 230 mg) in DMF (2 mL) CDI (1 mmol, 162 mg) was added, and the mixture was stirred at ambient temperature for 1 h, then 3-(3,4-dihydroisoquinolin-2(1H)-yl)propan-1-amine (1 mmol, 190.28 mg) was added. The mixture was stirred at ambient temperature overnight. The solvent was removed under reduced pressure, diluted with dichloromethane and washed with 5% aqueous solution Na₂CO₃. Layers were separated, the organic one dried over Na₂SO₄, filtered and concentrated under reduced pressure. The obtained residue was purified by column chromatography on silica gel to yield 1-(4-Cyanophenyl)-N-(3-(3,4-dihydroisoquinolin-2(1H)-yl)propyl)piperidine-4-carboxamide as white solid (369 mg, 92%). MS: m/z=403 [M+H]⁺.

Compound 2: N-(3-(3,4-dihydroisoquinolin-2(1H)-yl)propyl)-1-(4-(trifluoromethyl)phenyl)piperidine-4-carboxamide Compound 8: 1-(5-cyanopyridin-2-yl)-N-(2-(3,4-dihydroisoquinolin-2(1H)-yl)ethyl)piperidine-4-carboxamide

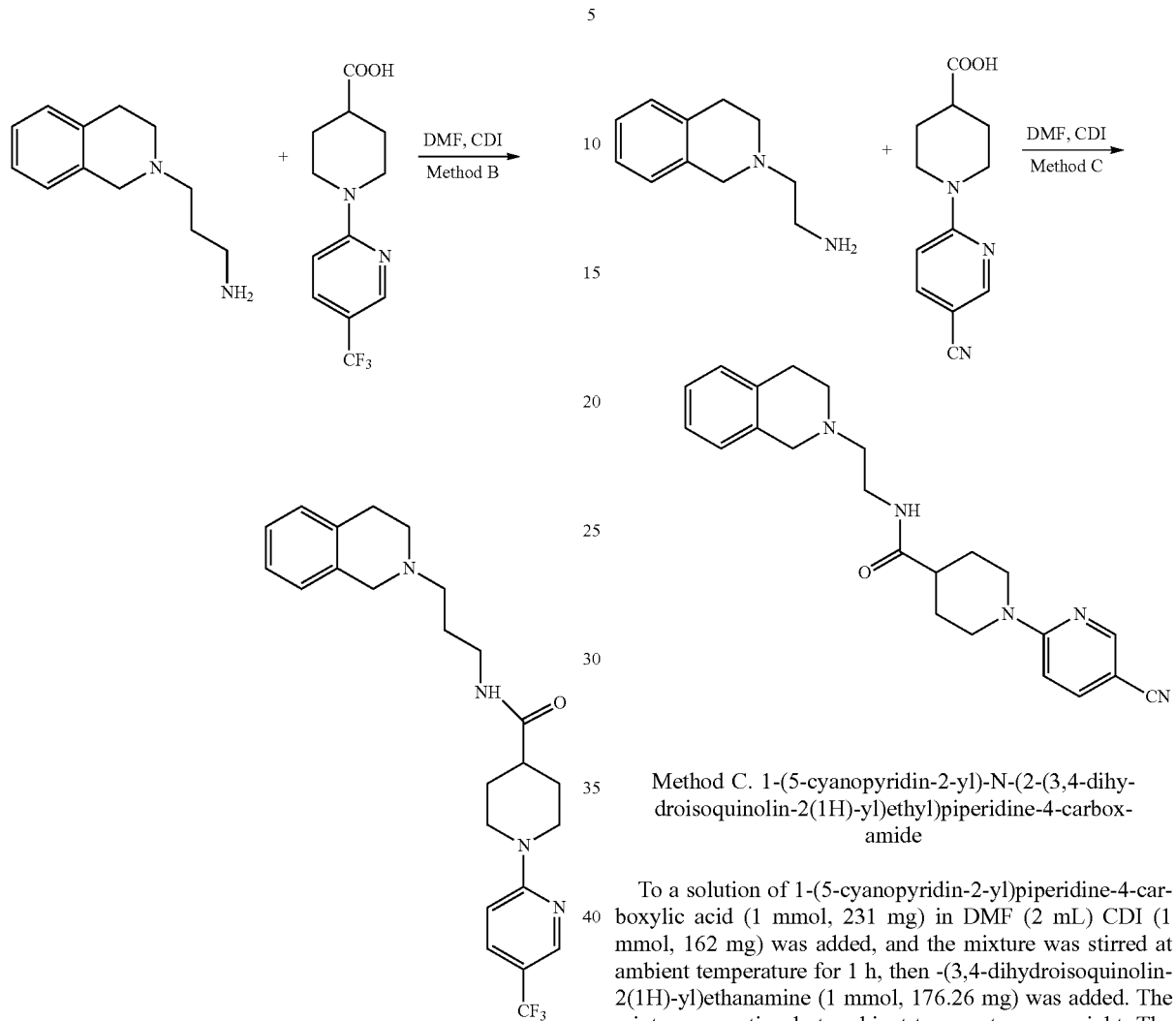

Method B. N-(3-(3,4-dihydroisoquinolin-2(1H)-yl)propyl)-1-(5-(trifluoromethyl)pyridin-2-yl)piperidine-4-carboxamide To a solution of 1-(5-(trifluoromethyl)pyridin-2-yl)piperidine-4-carboxylic acid (1 mmol, 274 mg) in DMF (2 mL) CDI (1 mmol, 162 mg) was added, and the mixture was stirred at ambient temperature for 1 h, then 3-(3,4-dihydroisoquinolin-2(1H)-yl)propan-1-amine (1 mmol, 190.28 mg) was added. The mixture was stirred at ambient temperature overnight. The solvent was removed under reduced pressure, diluted with dichloromethane and washed with 5% aqueous solution Na$_2$CO$_3$. Layers were separated, the organic one dried over Na$_2$SO$_4$, filtered and concentrated under reduced pressure. The obtained residue was purified by column chromatography on silica gel to yield N-(3-(3,4-dihydroisoquinolin-2(1H)-yl)propyl)-1-(5-(trifluoromethyl)pyridin-2-yl)piperidine-4-carboxamide as white solid (428 mg, 96%). MS: m/z=447 [M+H]$^+$.

Method C. 1-(5-cyanopyridin-2-yl)-N-(2-(3,4-dihydroisoquinolin-2(1H)-yl)ethyl)piperidine-4-carboxamide To a solution of 1-(5-cyanopyridin-2-yl)piperidine-4-carboxylic acid (1 mmol, 231 mg) in DMF (2 mL) CDI (1 mmol, 162 mg) was added, and the mixture was stirred at ambient temperature for 1 h, then -(3,4-dihydroisoquinolin-2(1H)-yl)ethanamine (1 mmol, 176.26 mg) was added. The mixture was stirred at ambient temperature overnight. The solvent was removed under reduced pressure, diluted with dichloromethane and washed with 5% aqueous solution Na$_2$CO$_3$. Layers were separated, the organic one dried over Na$_2$SO$_4$, filtered and concentrated under reduced pressure. The obtained residue was purified by column chromatography on silica gel to yield 1-(5-cyanopyridin-2-yl)-N-(2-(3,4-dihydroisoquinolin-2(1H)-yl)ethyl)piperidine-4-carboxamide as white solid (362 mg, 93%). MS: m/z=390 [M+H]$^+$.

Compound 10: 1-(4-cyano-2-fluorophenyl)-N-(2-(3,4-dihydroisoquinolin-2(1H)-yl)ethyl)piperidine-3-carboxamide

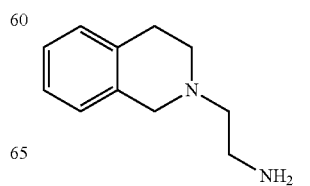

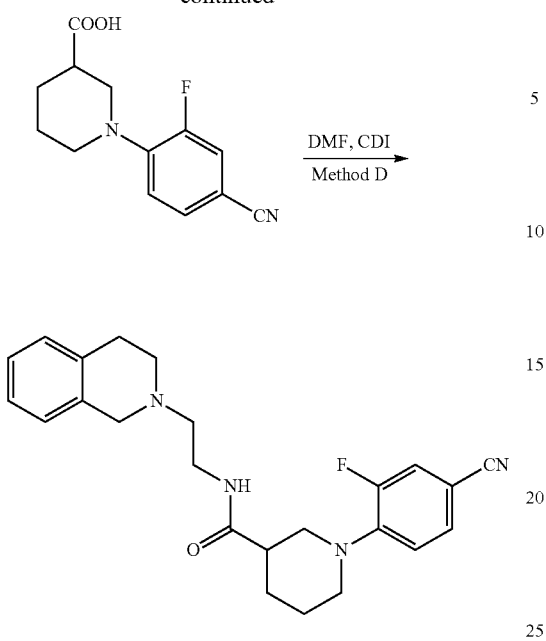

Method D: 1-(4-cyano-2-fluorophenyl)-N-(2-(3,4-dihydroisoquinolin-2(1H)-yl)ethyl)piperidine-3-carboxamide To a solution of 1-(4-cyano-2-fluorophenyl)piperidine-3-carboxylic acid (1 mmol, 248 mg) in DMF (2 mL) CDI (1 mmol, 162 mg) was added, and the mixture was stirred at ambient temperature for 1 h, then -(3,4-dihydroisoquinolin-2(1H)-yl)ethanamine (1 mmol, 176 mg) was added. The mixture was stirred at ambient temperature overnight. The solvent was removed under reduced pressure, diluted with dichloromethane and washed with 5% aqueous solution Na₂CO₃. Layers were separated, the organic one dried over Na₂SO₄, filtered and concentrated under reduced pressure. The obtained residue was purified by column chromatography on silica gel to yield 1-(4-cyano-2-fluorophenyl)-N-(2-(3,4-dihydroisoquinolin-2(1H)-yl)ethyl)piperidine-3-carboxamide as yellowish solid (394 mg, 97%). MS: m/z=407 [M+H]⁺.

Compound 11. 1-(4-cyanophenyl)-N-(2-(indolin-1-yl)ethyl)piperidine-4-carboxamide

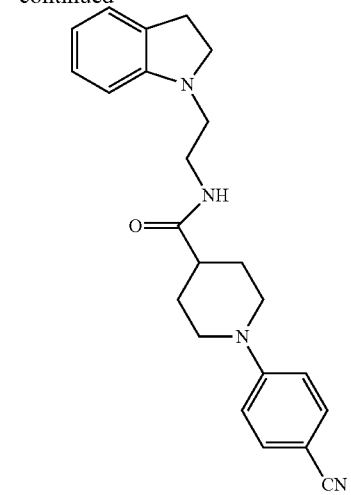

Method E: 1-(4-cyanophenyl)-N-(2-(indolin-1-yl)ethyl)piperidine-4-carboxamide To a solution of 1-(4-cyanophenyl)piperidine-4-carboxylic acid (1 mmol, 230 mg) in DMF (2 mL) CDI (1 mmol, 162 mg) was added, and the mixture was stirred at ambient temperature for 1 h, then 2-(indolin-1-yl)ethanamine (1 mmol, 162 mg) was added. The mixture was stirred at ambient temperature overnight. The solvent was removed under reduced pressure, diluted with dichloromethane and washed with 5% aqueous solution Na₂CO₃. Layers were separated, the organic one dried over Na₂SO₄, filtered and concentrated under reduced pressure. The obtained residue was purified by column chromatography on silica gel to yield 1-(4-cyanophenyl)-N-(2-(indolin-1-yl)ethyl)piperidine-4-carboxamide as white solid (340 mg, 91%). MS: m/z=375 [M+H]⁺.

Compound 17: N-(3-(indolin-1-yl)propyl)-1-(5-(trifluoromethyl)pyridin-2-yl)piperidine-4-carboxamide

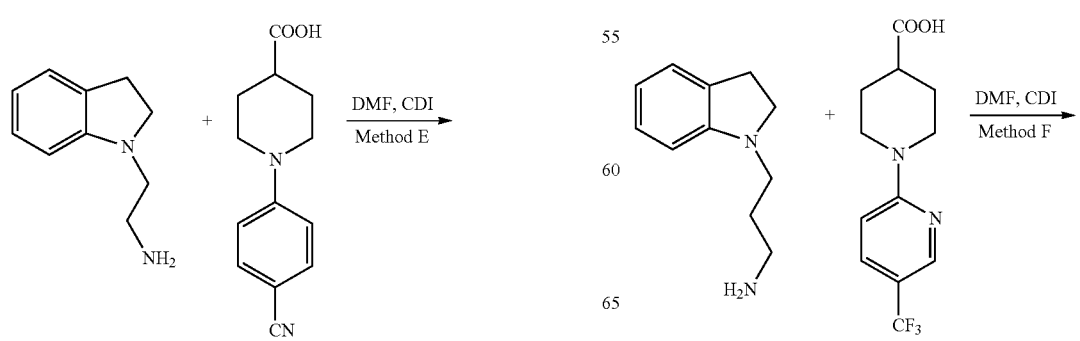

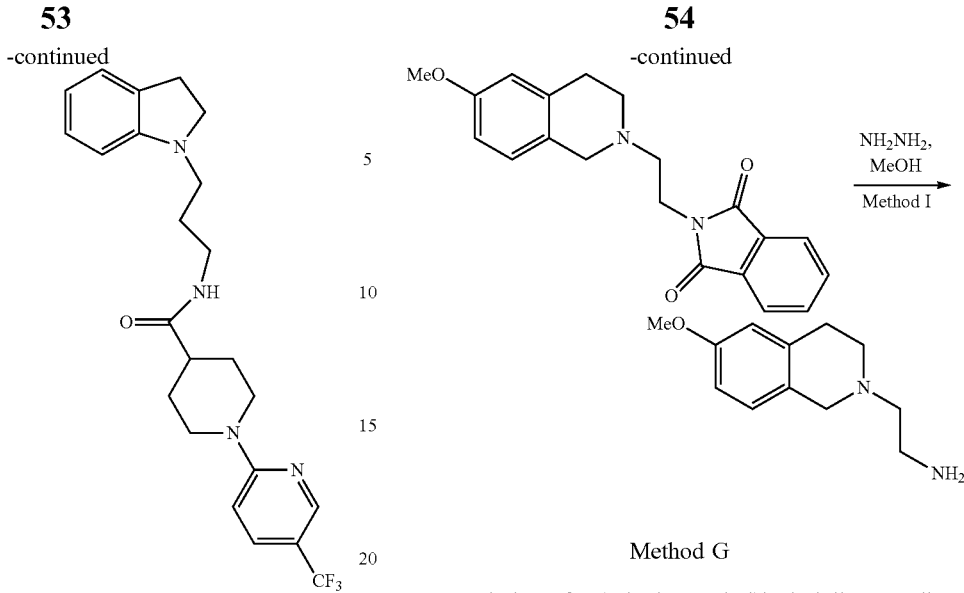

Method F: N-(3-(indolin-1-yl)propyl)-1-(5-(trifluoromethyl)pyridin-2-yl)piperidine-4-carboxamide To a solution of 1-(5-(trifluoromethyl)pyridin-2-yl)piperidine-4-carboxylic acid (1 mmol, 274 mg) in DMF (2 mL) CDI (1 mmol, 162 mg) was added, and the mixture was stirred at ambient temperature for 1 h, then 3-(indolin-1-yl)propan-1-amine (1 mmol, 176 mg) was added. The mixture was stirred at ambient temperature overnight. The solvent was removed under reduced pressure, diluted with dichloromethane and washed with 5% aqueous solution $Na_2CO_3$. Layers were separated, the organic one dried over $Na_2SO_4$, filtered and concentrated under reduced pressure. The obtained residue was purified by column chromatography on silica gel to yield N-(3-(indolin-1-yl)propyl)-1-(5-(trifluoromethyl)pyridin-2-yl)piperidine-4-carboxamide as white solid (414 mg, 96%). MS: m/z=433 [M+H]$^+$.

Intermediate 1: 2-(6-methoxy-3,4-dihydroisoquinolin-2(1H)-yl)ethanamine

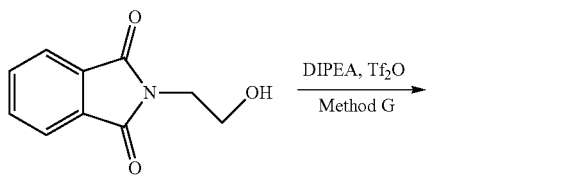

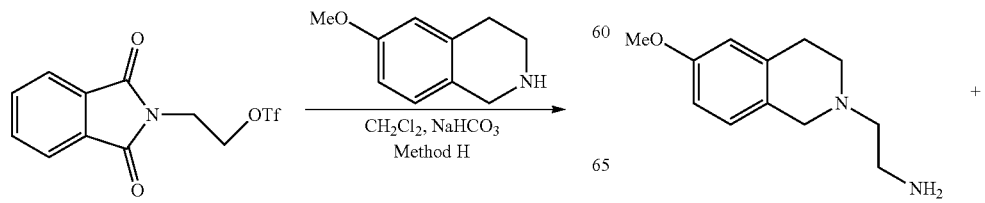

Method G

To a solution of 2-(2-hydroxyethyl)isoindoline-1,3-dione (10 mmol, 1.91 g) and DIPEA (10 mmol, 1.29 g) in $CH_2Cl_2$, trifluoromethanesulfonic anhydride (1.15 eq, 3.25 g) dropwise were added at 5° C. The mixture was stirred at room temperature for 1 h. After this time, the mixture was washed with 5% aqueous solution of $NaHCO_3$ and water. Layers were separated, the organic one dried over $Na_2SO_4$ and evaporated in vacuo to yield 2-(1,3-dioxoisoindolin-2-yl) ethyl trifluoromethanesulfonate as yellow oil (2.94 g, 92%). MS: m/z=324 [M+H]$^+$.

Method H

To a solution of 2-(1,3-dioxoisoindolin-2-yl)ethyl trifluoromethanesulfonate (5 mmol, 1.62 g) in $CH_2Cl_2$ (100 ml) 6-methoxy-1,2,3,4-tetrahydroisoquinoline (0.8 eq, 0.65 g) and saturated solution of $NaHCO_3$ in water (100 ml) were added. The mixture was stirred at room temperature for 12 h. After this time, the mixture was washed with water. Layers were separated, the organic one dried over $Na_2SO_4$ and evaporate to give crude product of 2-(2-(6-methoxy-3,4-dihydroisoquinolin-2(1H)-yl)ethyl)isoindoline-1,3-dione.

Method I

To a solution of crude 2-(2-(6-methoxy-3,4-dihydroisoquinolin-2(1H)-yl)ethyl)isoindoline-1,3-dione in MeOH (200 ml) $N_2H_4 \cdot H_2O$ (25 mmol, 1.71 g) was added. The mixture was stirred at room temperature for 12 h. A pellet developed gradually and was filtered. The solvent was evaporated. The obtained residue was purified by column chromatography on silica gel to give 2-(6-methoxy-3,4-dihydroisoquinolin-2(M)-yl)ethanamine as white solid (0.93 g, 90%). MS: m/z=207 [M+H]$^+$ Compound 21: 1-(4-cyanophenyl)-N-(2-(6-methoxy-3,4-dihydroisoquinolin-2(1H)-yl)ethyl) piperidine-4-carboxamide

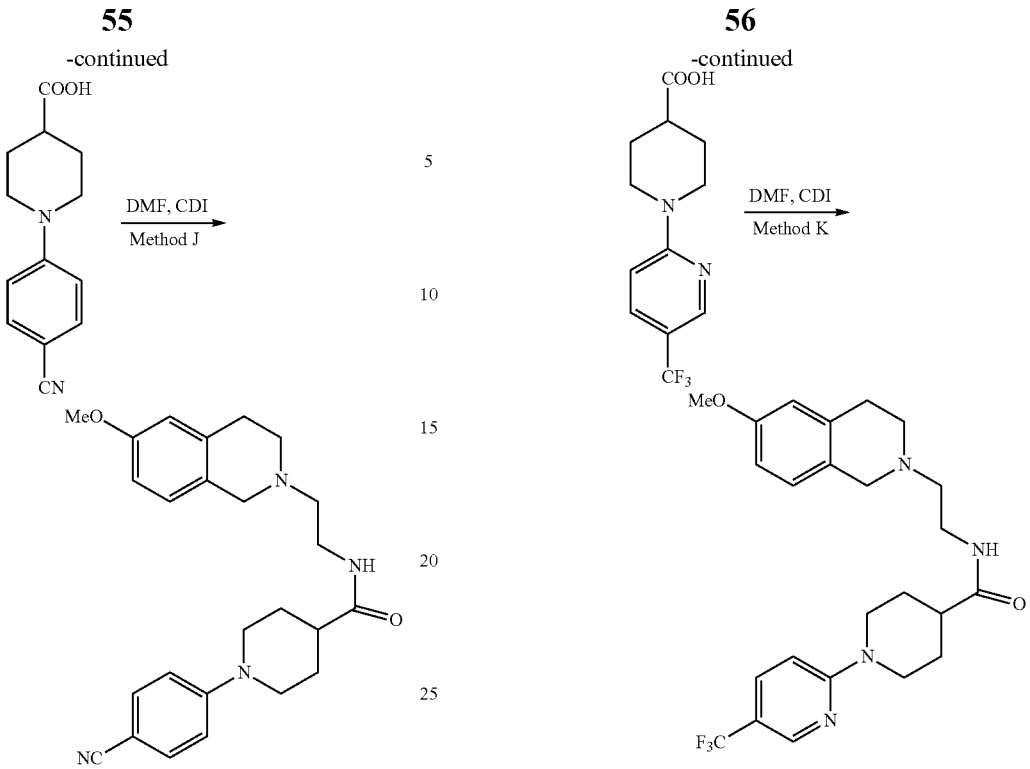

Method J: 1-(4-cyanophenyl)-N-(2-(6-methoxy-3,4-dihydroisoquinolin-2(1H)-yl)ethyl)piperidine-4-carboxamide To a solution of 1-(4-cyanophenyl)piperidine-4-carboxylic acid (1 mmol, 230 mg) in DMF (2 mL) CDI (1 mmol, 162 mg) was added, and the mixture was stirred at ambient temperature for 1 h, then 2-(6-methoxy-3,4-dihydroisoquinolin-2(1H)-yl)ethanamine (1 mmol, 206 mg) was added. The mixture was stirred at ambient temperature overnight. The solvent was removed under reduced pressure, diluted with dichloromethane and washed with 5% aqueous solution Na$_2$CO$_3$. Layers were separated, the organic one dried over Na$_2$SO$_4$, filtered and concentrated under reduced pressure. The obtained residue was purified by column chromatography on silica gel to yield 1-(4-cyanophenyl)-N-(2-(6-methoxy-3,4-dihydroisoquinolin-2(1H)-yl)ethyl)piperidine-4-carboxamide as white solid (397 mg, 95%). MS: m/z=419 [M+H]$^+$.

Compound 22: N-(2-(6-methoxy-3,4-dihydroisoquinolin-2(1H)-yl)ethyl)-1-(5-(trifluoromethyl)pyridin-2-yl)piperidine-4-carboxamide

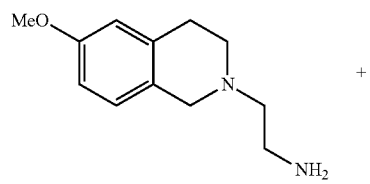

Method K: N-(2-(6-methoxy-3,4-dihydroisoquinolin-2(1H)-yl)ethyl)-1-(5-(trifluoromethyl)pyridin-2-yl)piperidine-4-carboxamide To a solution of 1-(5-(trifluoromethyl)pyridin-2-yl)piperidine-4-carboxylic acid (1 mmol, 274 mg) in DMF (2 mL) CDI (1 mmol, 162 mg) was added, and the mixture was stirred at ambient temperature for 1 h, then 2-(6-methoxy-3,4-dihydroisoquinolin-2(1H)-yl)ethanamine (1 mmol, 206 mg) was added. The mixture was stirred at ambient temperature overnight. The solvent was removed under reduced pressure, diluted with dichloromethane and washed with 5% aqueous solution Na$_2$CO$_3$. Layers were separated, the organic one dried over Na$_2$SO$_4$, filtered and concentrated under reduced pressure. The obtained residue was purified by column chromatography on silica gel to yield N-(2-(6-methoxy-3,4-dihydroisoquinolin-2(1H)-yl)ethyl)-1-(5-(trifluoromethyl)pyridin-2-yl)piperidine-4-carboxamide as white solid (430 mg, 93%). MS: m/z=463 [M+H]$^+$.

Intermediate 2: 3-(6-methoxy-3,4-dihydroisoquinolin-2(1H)-yl)propan-1-amine

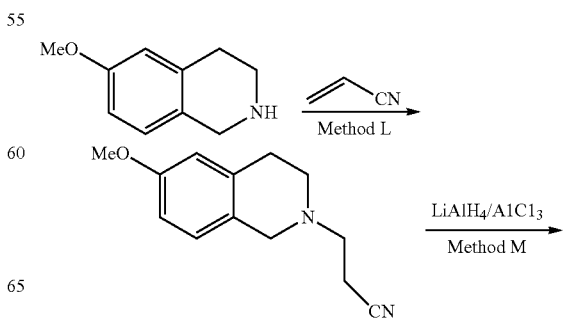

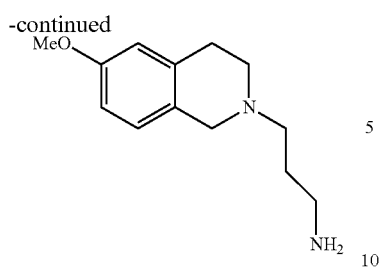

Method L

6-Methoxy-1,2,3,4-tetrahydroisoquinoline hydrochloride (10 mmol, 1.99 g) was dissolved in ethanol (100 mL) and treated with Et₃N (10 mmol, 1.01 g) and an access of acrylonitrile (30 mmol, 1.59 g). The mixture was heated to reflux for 5 h. The volatiles were removed under reduced pressure, and the residue was portioned between CH$_2$Cl$_2$ and water. The organic layer was washed with brine, dried (Na$_2$SO$_4$), and filtered. Evaporation of the solvent yielded the crude product, which could be purified by chromatography to give 3-(6-methoxy-3,4-dihydroisoquinolin-2(1H)-yl)propanenitrile as white solid (2.07 g, 96%). MS: m/z=217 [M+H]⁺.

Method M

A solution of 3-(6-methoxy-3,4-dihydroisoquinolin-2 (1H)-yl)propanenitrile (5 mmol, 1.08 g) in THF (10 ml) was added dropwise to a freshly prepared suspension of AlCl$_3$ (9 mmol, 1.20 g) and LiAlH$_4$ (9.25 mmol, 0.35 g) in THF (dry, 250 mL) under nitrogen atmosphere. The mixture was allowed to stir at room temperature overnight. Workup was initiated by careful subsequent addition of water (5 mmol, 0.1 mL), NaOH (1N, 5 mL), and another portion of water (20 mmol, 0.4 mL) and filtration of the salts thus formed over Celite. The clear solution was dried (Na$_2$SO$_4$) and concentrated in vacuo to yield 3-(6-methoxy-3,4-dihydroisoquinolin-2(1H)-yl)propan-1-amine as white solid (0.94 g, 86%). MS: m/z=221 [M+H]⁺.

Compound 29: 1-(4-cyanophenyl)-N-(3-(6-methoxy-3,4-dihydroisoquinolin-2(1H)-yl)propyl)piperidine-3-carboxamide

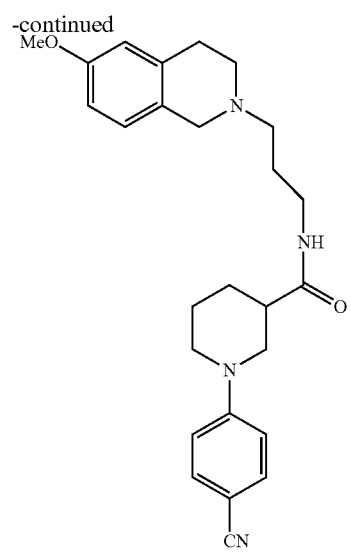

Method N: 1-(4-cyanophenyl)-N-(3-(6-methoxy-3,4-dihydroisoquinolin-2(1H)-yl)propyl)piperidine-3-carboxamide To a solution of 1-(4-cyanophenyl)piperidine-3-carboxylic acid (1 mmol, 230 mg) in DMF (2 mL) CDI (1 mmol, 162 mg) was added, and the mixture was stirred at ambient temperature for 1 h, then 3-(6-methoxy-3,4-dihydroisoquinolin-2(1H)-yl)propan-1-amine (1 mmol, 220 mg) was added. The mixture was stirred at ambient temperature overnight. The solvent was removed under reduced pressure, diluted with dichloromethane and washed with 5% aqueous solution Na$_2$CO$_3$. Layers were separated, the organic one dried over Na$_2$SO$_4$, filtered and concentrated under reduced pressure. The obtained residue was purified by column chromatography on silica gel to yield 1-(4-cyanophenyl)-N-(3-(6-methoxy-3,4-dihydroisoquinolin-2(1H)-yl)propyl)piperidine-3-carboxamide as white solid (419 mg, 97%). MS: m/z=433 [M+H]⁺.

Compound 30: 1-(4-cyano-2-fluorophenyl)-N-(3-(6-methoxy-3,4-dihydroisoquinolin-2(1H)-yl)propyl)piperidine-3-carboxamide

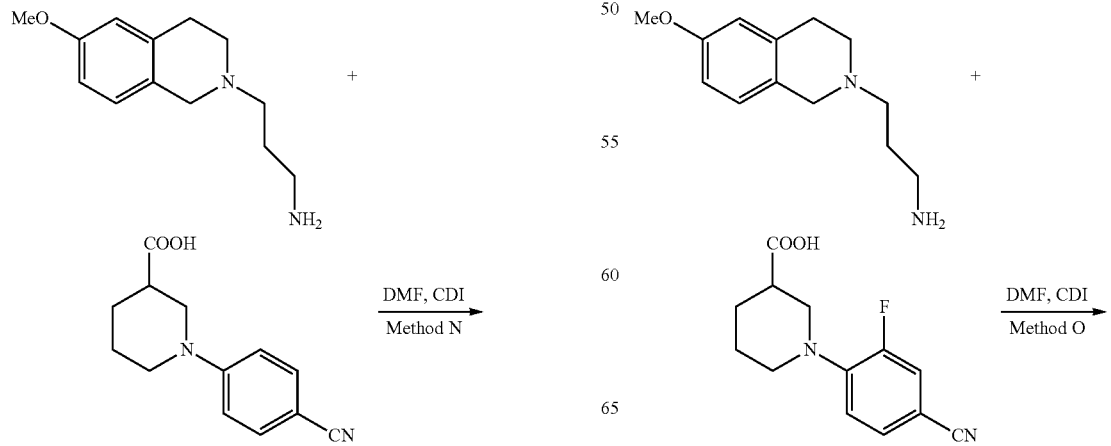

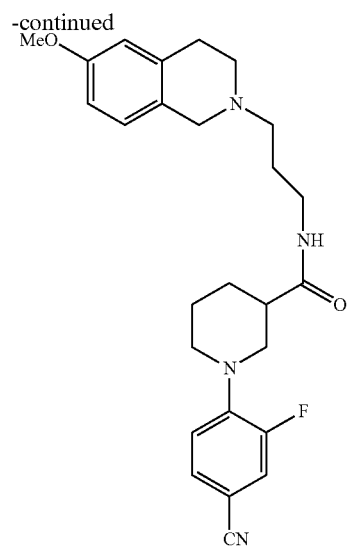

Method O: 1-(4-cyano-2-fluorophenyl)-N-(3-(6-methoxy-3,4-dihydroisoquinolin-2(1H)-yl)propyl)piperidine-3-carboxamide To a solution of 1-(4-cyano-2-fluorophenyl)piperidine-3-carboxylic acid (1 mmol, 248 mg) in DMF (2 mL) CDI (1 mmol, 162 mg) was added, and the mixture was stirred at ambient temperature for 1 h, then 3-(6-methoxy-3,4-dihydroisoquinolin-2(1H)-yl)propan-1-amine (1 mmol, 220 mg) was added. The mixture was stirred at ambient temperature overnight. The solvent was removed under reduced pressure, diluted with dichloromethane and washed with 5% aqueous solution $Na_2CO_3$. Layers were separated, the organic one dried over $Na_2SO_4$, filtered and concentrated under reduced pressure. The obtained residue was purified by column chromatography on silica gel to yield 1-(4-cyano-2-fluorophenyl)-N-(3-(6-methoxy-3,4-dihydroisoquinolin-2(1H)-yl)propyl)piperidine-3-carboxamide as white solid (405 mg, 90%). MS: m/z=451 [M+H]$^+$.

Example 2

Select compounds were used for screening as agonists for human TLR2, TLR3, TLR4, TLR5, TLR7, TLR8, or TLR9. The screened compounds include: compound 1 (i.e., INS020_001); compound 4 (i.e., INS020_002); compound 9 (i.e., INS020_003); compound 15 (i.e., INS020_004); and compound 25 (i.e., INS020_005). Each compound was screened for potential antagonistic effect on various human receptors known to recognize pathogen associated molecular patterns (PAMPs).

Samples and controls are tested in duplicate on recombinant HEK-293 cell lines. These cell lines functionally over express a given TLR protein as well as a reporter gene which is a secreted alkaline phosphatase (SEAP). The production of this reporter gene is driven by a NF-KB inducible promoter. The magnitude of activation is represented in optical density values (OD). A recombinant HEK-293 cell line for the reporter gene only was used as a negative control for the TLR cell lines (mentioned as TLR– in the data). This negative control cell line does not over-express any TLR gene, but the reporter gene only (alkaline phosphatase). This reporter gene is directly inducible with TNFα. The non-induced value for each clone is the background signal of the cell line.

In a 96-well (200 µl total volume) containing the appropriate cells (50,000-80,000 cells/well), 20 µL of the test article is added to the well and is incubated with the cells at 37° C. with 5% $CO_2$ for 3 hours prior to the addition of the agonist control. After further incubation with the agonist at 37° C. with 5% $CO_2$ for 16-24 hours, the optical density (OD) is read at 630.

Following is the list of different ligands used as positive induction controls in this study:

| Receptor | Agonist Ligand | Final Concentration |
|---|---|---|
| hTLR2 | Pam2CSK4 | 1 ng/ml |
| hTLR3 | Poly I:C (HMW) | 1 µg/ml |
| hTLR4 | LPS-EK - Standard LPS from *E. coli* K12 | 10 ng/ml |
| hTLR5 | FLA-ST - Standard flagellin from *S. thyphimurium* | 1 µg/ml |
| hTLR7 | R848 | 1 µg/ml |
| hTLR8 | TL8-506 | 1 µg/ml |
| hTLR9 | ODN 2006 | 10 µg/ml |

The control cell line (TLR-) is activated by TNFα.

Compound(s) Tested:

| Test article | Weight | Reconstitution volume |
|---|---|---|
| INS020_001 | 2.29 mg/vial | 2.84 ml |
| INS020_002 | 2.22 mg/vial | 2.76 ml |
| INS020_003 | 2.06 mg/vial | 2.65 ml |
| INS020_004 | 2.24 mg/vial | 2.85 ml |
| INS020_005 | 2.39 mg/vial | 2.74 ml |
| INS020_100 | 1.49 mg/vial | 2.80 ml |

Preparation of Test Article:

Samples were reconstituted in DMSO with the volume noted above to obtain a 2 mM stock solution. Stock solution was further diluted with complete DMEM 20-fold to obtain a solution at 100 µM. 20 µl of the diluted sample is used to treat the cells in a 200 µl of final reaction volume. The sample has therefore been tested at 10 µl final concentration.

Activation of the SEAP reporter is detected as OD value. OD value is subtracted by average non-induced (NI) value. The NI subtracted duplicates are averaged and presented in a histogram format hereafter. The values in the tables are the corresponding OD values for the Agonist and the Compound (e.g., shown as compound number).

| TLR | TLR | TLR2 | TLR3 | TLR4 | TLR5 | TLR7 | TLR8 | TLR9 |
|---|---|---|---|---|---|---|---|---|
| Agonist | 1.71 | 2.03 | 1.58 | 1.65 | 2.51 | 2.05 | 2.32 | 1.72 |
| 1 | 1.22 | 1.85 | 1.21 | 1.48 | 2.41 | 1.73 | 2.24 | 0.06 |
| Agonist | 1.71 | 2.03 | 1.58 | 1.65 | 2.51 | 2.05 | 2.32 | 1.72 |
| 4 | 1.35 | 1.8 | 1.36 | 1.6 | 2.21 | 1.78 | 2.16 | 0.14 |
| Agonist | 1.71 | 2.03 | 1.58 | 1.65 | 2.51 | 2.05 | 2.32 | 1.72 |
| 9 | 1.25 | 2.02 | 1.37 | 1.54 | 2.16 | 1.73 | 2.17 | 0.32 |

-continued

| | | | | | | | | |
|---|---|---|---|---|---|---|---|---|
| Agonist | 1.71 | 2.03 | 1.58 | 1.65 | 2.51 | 2.05 | 2.32 | 1.72 |
| 15 | 1.17 | 2.15 | 1.37 | 1.5 | 2.45 | 1.72 | 2.25 | 1.51 |
| Agonist | 1.71 | 2.03 | 1.58 | 1.65 | 2.51 | 2.05 | 2.32 | 1.72 |
| 25 | 1.12 | 2.04 | 1.35 | 1.47 | 2.41 | 1.73 | 2.28 | 0.34 |
| Agonist | 1.71 | 2.03 | 1.58 | 1.65 | 2.51 | 2.05 | 2.32 | 1.72 |
| Control | 1.64 | 2.16 | 1.52 | 1.95 | 2.22 | −0.01 | 0.01 | 0.10 |

| | TLR | TLR2 | TLR3 | TLR4 | TLR5 | TLR7 | TLR8 | TLR9 |
|---|---|---|---|---|---|---|---|---|
| Agonist | 100% | 100% | 100% | 100% | 100% | 100% | 100% | 100% |
| 1 | 71% | 91% | 77% | 90% | 96% | 84% | 97% | 4% |
| 4 | 79% | 88% | 86% | 97% | 88% | 87% | 93% | 8% |
| 9 | 73% | 99% | 87% | 93% | 86% | 84% | 94% | 18% |
| 15 | 68% | 106% | 87% | 91% | 98% | 84% | 97% | 88% |
| 25 | 65% | 100% | 86% | 89% | 96% | 84% | 98% | 20% |
| Control | 96% | 106% | 96% | 118% | 88% | 0% | 0% | 6% |

At 10 μM, test articles Compound 1, Compound 4, Compound 9, and Compound 25 show specific and significant antagonistic effect on human TLR9. At 10 μM, the control is shown to be a general agonist for TLR7, TLR8 and TLR9. Thus, specific TLR9 inhibitors that are selective for TLR9 over other TLRs include Compound 1, Compound 4, Compound 9, and Compound 25.

The invention claimed is:

1. A method for inhibiting TLR9 activity, the method comprising:
administering a compound to a TLR9 in an amount sufficient to inhibit activity thereof, the compound having a structure of Formula (I), or a stereoisomeric form, a mixture of stereoisomeric forms, or pharmaceutically acceptable salts thereof,

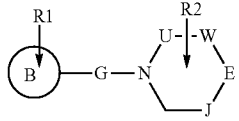

(I)

wherein,
ring B is a substituted monocycle containing 3-7 atoms, the monocycle being selected from an aryl or heteroaryl, wherein the heteroaryl has from 1 to 4 heteroatoms, which are independently selected from nitrogen, oxygen, and sulfur;
G represents a substituted or unsubstituted $C_0$-$C_5$ alkylene;
one of W, U, E and J represents CR-T and the rest of W, U, and J are independently absent or independently represent $CR_2$ or NR;
T represents:

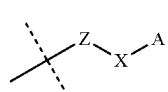

(T₀)

wherein,
Z is selected from —O—C(NR)— and —(NR)C—O—;
X represents —($CH_2$—)$_n$ wherein n=1 to 12, thereby forming an alkylene chain, wherein the alkylene chain is optionally substituted with halogen, $C_1$-$C_{20}$ alkyl, $C_2$-$C_{10}$ alkenyl, $C_2$-$C_{10}$ alkynyl, halogenated $C_1$-$C_{10}$ alkyl, hydroxy $C_1$-$C_{10}$ alkyl, or $C_1$-$C_{10}$alkoxy;
A is 3 to 8 membered heterocyclyl fused with an aryl or heteroaryl, which can be unsubstituted or substituted with one or more R substituents;
$R_1$ is one or more of, independently of each other, H, halogen, halogenated $C_1$-$C_{10}$ alkyl, hydroxy $C_1$-$C_{10}$ alkyl, $C_1$-$C_{10}$ alkoxy, or —CN;
$R_2$ is one or more of, independently of each other, H, $C_1$-$C_{20}$ alkyl, halogenated $C_1$-$C_{20}$ alkyl, —OR, —SR, or —CN; and
each R is independently H, $C_1$-$C_{20}$ alkyl, $C_2$-$C_{20}$ alkenyl, $C_2$-$C_{20}$ alkynyl, hydroxy $C_1$-$C_{10}$ alkyl, $C_1$-$C_{10}$ alkoxy, halogenated $C_1$-$C_{20}$ alkyl, halogen, —OH, —$NO_2$, —CN, —COOH, —CHO, —$SO_3H$, —$SO_2R$, —SOR, —$NH_2$, —NHR, —$NR_2$, $CHal_3$, —NHCO($C_1$-$C_{10}$)alkyl, —CONHR, —C(O)R, —$CO_2R$, —C(O)N(R)$_2$, —NRC(O)R, —NRC(O)N(R)$_2$, —$NRSO_2R$.

2. The method according to claim 1, wherein the compound is administered to the TLR9 in vitro.

3. The method according to claim 1, wherein the compound is administered to the TLR9 in vivo.

4. The method according to claim 1, wherein the compound is administered to a subject having the TLR9, wherein the subject is susceptible or has a disease or disorder mediated by the TLR9.

5. The method of claim 4, wherein the subject has a includes at least one of: a disorder or disease associated with the over-stimulation of the subject's immune system by microbes; interferon-mediated diseases; or inflammatory cytokine-mediated inflammation diseases.

6. The method according to claim 5, further comprising treating the disorder or disease associated with the over-stimulation of the subject's immune system by microbes.

7. The method according to claim 5, further comprising treating the interferon-mediated disease.

8. The method according to claim 5, further comprising treating the inflammatory cytokine-mediated inflammation diseases.

9. The method of claim 4, further comprising treating at least one of: antiphospholipid syndrome, autoimmune hepatitis, autoimmune myocarditis, autoimmune orchitis, autoimmune pancreatitis, autoimmune retinopathy, rheumatoid arthritis, psoriatic arthritis, osteoarthritis, systemic Lupus Erythematosus, lupus nephritis, osteoporosis, systemic sclerosis, multiple sclerosis, psoriasis, diabetes, inflammatory bowel disease (Crohn's Disease and Ulcerative Colitis), Hyperimmunoglobulinemia D, periodic fever syndrome, systemic juvenile idiopathic arthritis, sepsis, atherosclerosis, Celiac disease, Sjogren's Syndrome, Alzheimer's disease, Parkinson's disease, or cancer.

10. The method of claim 9, wherein the cancer is selected from colorectal cancer, breast cancer, ovarian carcinoma, pancreatic cancer, lung cancer, renal cell carcinoma, cervical cancer and multiple myeloma.

11. The method of claim 1, further comprising inhibiting TLR9 activity with the compound.

12. The method of claim 4, further comprising inhibiting inflammation in the subject with the compound.

13. The method of claim 4, further comprising inhibiting activation of an immune system of the subject with the compound.

14. The method of claim 1, further comprising contacting cells with the compound, wherein the cells express the TLR9.

15. The method of claim 1, further comprising:
the compound having a structure of Formula (III), or a stereoisomeric form, a mixture of stereoisomeric forms, or pharmaceutically acceptable salts thereof,

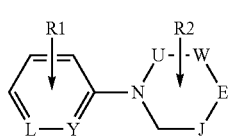

(III)

wherein,
Y and L are independently CR or CH,
one of W, U, E and J represents CH(T) and the rest of W, U, and J are independently absent or independently represent $CH_2$;
T represents:

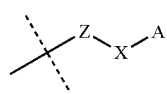

($T_0$)

wherein,
Z is selected from —O—C(NR)— and —(NR)C—O—;
X represents (—$CH_2$—)$_n$ wherein n=1 to 24, thereby forming an alkylene chain, wherein the alkylene chain is optionally substituted with halogen, $C_1$-$C_{20}$ alkyl, $C_2$-$C_{10}$ alkenyl, $C_2$-$C_{10}$ alkynyl, halogenated $C_1$-$C_{10}$ alkyl, hydroxy $C_1$-$C_{10}$ alkyl, or $C_1$-$C_{10}$ alkoxy;
A represents:

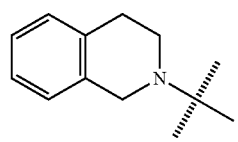

A1

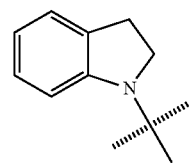

A2

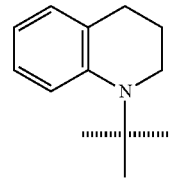

A3

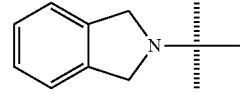

A4 any one of A1, A2, A3, or A4 is unsubstituted or substituted with one or more R groups;

$R_1$ is one or more of, independently of each other, H, halogen, halogenated $C_1$-$C_{10}$ alkyl, hydroxy $C_1$-$C_{10}$ alkyl, $C_1$-$C_{10}$ alkoxy, or —CN;

$R_2$ is one or more of, independently of each other, H, $C_1$-$C_{20}$ alkyl, halogenated $C_1$-$C_{20}$ alkyl, —OR, —SR, or —CN; and each R is independently H, $C_1$-$C_{20}$ alkyl, $C_2$-$C_{20}$ alkenyl, $C_2$-$C_{20}$ alkynyl, hydroxy $C_1$-$C_{10}$ alkyl, alkoxy, halogenated $C_1$-$C_{20}$ alkyl, halogen, —OH, —$NO_2$, —CN, —COOH, —CHO, —$SO_3H$, —$SO_2R$, —SOR, —$NH_2$, —NHR, —$NR_2$, $CHal_3$, —NHCO($C_1$-$C_{10}$)alkyl (e.g., alkyl-amide), —CONHR, —C(O)R, —$CO_2R$, —C(O)N(R)$_2$, —NRC(O)R, —NRC(O)N(R)$_2$, —NR$SO_2$R.

16. The method of claim 15, wherein:
Y is CR and L is CH, $R_1$ is para position;
one of W, U, E and J represents CH(T) and the rest of W, U, and J are independently absent or independently represent $CH_2$;
X represents (—$CH_2$—)$_n$ wherein n=1, 2, or 3, thereby forming an alkylene chain;
A represents:

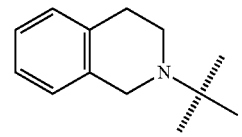

A1

A1 is unsubstituted or substituted with one or more R groups;

$R_1$ is one or more of, independently of each other, H, halogen, halogenated $C_1$-$C_{10}$ alkyl, hydroxy $C_1$-$C_{10}$ alkyl, $C_1$-$C_{10}$ alkoxy, or —CN;

$R_2$ is one or more of, independently of each other, H, $C_1$-$C_{20}$ alkyl, halogenated $C_1$-$C_{20}$ alkyl, —OR, —SR, or —CN; and each R is independently H, $C_1$-$C_{20}$ alkyl, $C_2$-$C_{20}$ alkenyl, $C_2$-$C_{20}$ alkynyl, hydroxy $C_1$-$C_{10}$ alkyl, $C_1$-$C_{10}$ alkoxy, halogenated $C_1$-$C_{20}$ alkyl, halogen, —OH, —$NO_2$, —CN.

17. The method of claim 1, the compound having a structure of Formula (IV), or a stereoisomeric form, a mixture of stereoisomeric forms, or pharmaceutically acceptable salts thereof, (IV)

wherein,
Y and L are independently CH or CR, wherein at least one of Y or L is CH;
G1 is CH₂ or absent;
each R is independently selected from H, halogen, $C_1$-$C_6$ alkyl, halogenated $C_1$-$C_6$ alkyl, hydroxy $C_1$-$C_6$ alkyl, $C_1$-$C_6$ alkoxy, or —CN; and
X represents (—CH₂—)$_n$, wherein n=2 or 3, thereby forming an alkylene chain.

18. The method of claim 17, the compound having a structure of Formula (VI), or a stereoisomeric form, a mixture of stereoisomeric forms, or pharmaceutically acceptable salts thereof, (VI)

wherein,
G1 is CH or absent;
X represents (—CH₂—)$_n$ wherein n=1 to 4, thereby forming an alkylene chain, the alkylene chain is optionally substituted with halogen, $C_1$-$C_6$ alkyl, $C_2$-$C_8$ alkenyl, $C_3$-$C_8$ cycloalkyl, $C_2$-$C_8$ alkynyl, halogenated $C_1$-$C_6$ alkyl, hydroxy $C_1$-$C_6$ alkyl, or $C_1$-$C_6$ alkoxy;
R3 is one or more of H, halogen, halogenated $C_1$-$C_{10}$ alkyl, hydroxy $C_1$-$C_{10}$ alkyl, $C_1$-$C_{10}$ alkoxy, or —CN;
R4 is one or more of H, halogen, halogenated $C_1$-$C_{10}$ alkyl, hydroxy $C_1$-$C_{10}$ alkyl, $C_1$-$C_{10}$ alkoxy, or —CN;
R5 is one or more of H, halogen, halogenated $C_1$-$C_{10}$ alkyl, hydroxy $C_1$-$C_{10}$ alkyl, or $C_1$-$C_{10}$ alkoxy.

19. The method of claim 18, wherein:
G1 is CH or absent;
X represents (—CH₂—)n wherein n=2 or 3, thereby forming an alkylene chain;
$R^3$ is —CN;
$R^4$ is one or more of H, halogen, or halogenated $C_1$-$C_{10}$ alkyl; and
$R^5$ is one or more of H, hydroxy $C_1$-$C_{10}$ alkyl, or $C_1$-$C_{10}$ alkoxy.

20. The method of claim 1, wherein the compound is selected from:

Compound 1

Compound 4

Compound 9

Compound 15 or

Compound 25
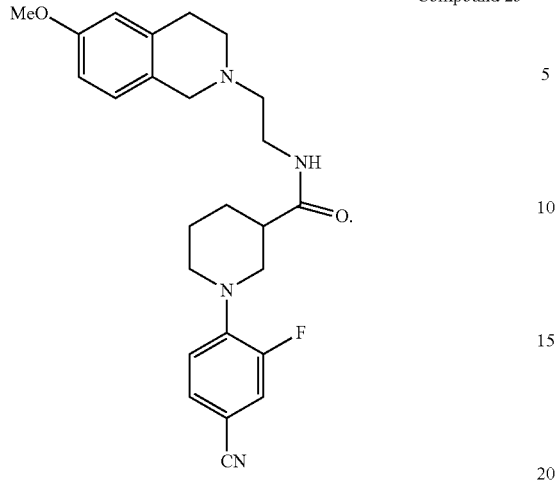
21. The method of claim 20, wherein the compound is selected from: Compound 1, Compound 4, Compound 9, or Compound 25.
* * * * *